United States Patent
Hariri

(10) Patent No.: US 7,311,904 B2
(45) Date of Patent: Dec. 25, 2007

(54) TISSUE MATRICES COMPRISING PLACENTAL STEM CELLS, AND METHODS OF MAKING THE SAME

(75) Inventor: Robert J. Hariri, Florham Park, NJ (US)

(73) Assignee: Anthrogenesis Corporation, Summit, NJ (US)

( * ) Notice: Subject to any disclaimer, the term of this patent is extended or adjusted under 35 U.S.C. 154(b) by 37 days.

(21) Appl. No.: 10/074,976

(22) Filed: Feb. 13, 2002

(65) Prior Publication Data

US 2002/0160510 A1 Oct. 31, 2002

Related U.S. Application Data

(60) Provisional application No. 60/268,560, filed on Feb. 14, 2001.

(51) Int. Cl.
*A01N 63/00* (2006.01)
(52) U.S. Cl. .................. 424/93.1; 435/325; 435/366; 435/1.1; 424/582; 424/583
(58) Field of Classification Search ............... 435/325, 435/376, 1.1, 379; 623/11.11
See application file for complete search history.

(56) References Cited

U.S. PATENT DOCUMENTS

| | | | |
|---|---|---|---|
| 4,060,081 A | 11/1977 | Yannas et al. | |
| 4,458,678 A | 7/1984 | Yannas et al. | |
| 4,485,097 A | 11/1984 | Bell | |
| 4,520,821 A | 6/1985 | Schmidt et al. | |
| 5,192,312 A | 3/1993 | Orton | |
| 5,192,553 A | 3/1993 | Boyse et al. | |
| 5,197,985 A | 3/1993 | Caplan et al. | |
| 5,226,914 A | 7/1993 | Caplan et al. | |
| 5,272,071 A | 12/1993 | Chappel | |
| 5,372,581 A | 12/1994 | Anderson | |
| 5,415,665 A | 5/1995 | Hessel et al. | |
| 5,437,994 A | 8/1995 | Emerson et al. | |
| 5,464,764 A | 11/1995 | Capecchi et al. | |
| 5,486,359 A | 1/1996 | Caplan et al. | |
| 5,487,992 A | 1/1996 | Capecchi et al. | |
| 5,591,625 A | 1/1997 | Gerson et al. | |
| 5,627,059 A | 5/1997 | Capecchi et al. | |
| 5,635,386 A | 6/1997 | Palsson et al. | |
| 5,646,043 A | 7/1997 | Emerson et al. | |
| 5,733,542 A | 3/1998 | Haynesworth et al. | |
| 5,736,396 A | 4/1998 | Bruder et al. | |
| 5,811,094 A | 9/1998 | Caplan et al. | |
| 5,827,740 A | 10/1998 | Pittenger | |
| 5,855,619 A | 1/1999 | Caplan et al. | |
| 5,899,936 A * | 5/1999 | Goldstein ............ 128/898 |
| 5,908,784 A | 6/1999 | Johnstone et al. | |
| 5,919,702 A | 7/1999 | Purchio et al. | |
| 5,942,225 A | 8/1999 | Bruder et al. | |
| 5,942,496 A | 8/1999 | Bonadio et al. | |
| 5,962,325 A * | 10/1999 | Naughton et al. ......... 435/395 |
| 6,010,696 A | 1/2000 | Caplan et al. | |
| 6,022,540 A | 2/2000 | Bruder et al. | |
| 6,030,836 A | 2/2000 | Thiede et al. | |
| 6,174,333 B1 | 1/2001 | Kadiyala et al. | |
| 6,225,119 B1 | 5/2001 | Qasba et al. | |
| 6,239,157 B1 | 5/2001 | Mbalaviele et al. | |
| 6,255,112 B1 | 7/2001 | Thiede et al. | |
| 6,261,549 B1 | 7/2001 | Fernandez et al. | |
| 6,281,012 B1 | 8/2001 | McIntosh et al. | |
| 6,322,784 B1 | 11/2001 | Pittenger et al. | |
| 6,326,198 B1 | 12/2001 | Emerson et al. | |
| 6,328,762 B1 * | 12/2001 | Anderson et al. .......... 623/1.41 |
| 6,328,960 B1 | 12/2001 | McIntosh et al. | |
| 6,337,387 B1 | 1/2002 | Sakano et al. | |
| 6,338,942 B2 | 1/2002 | Kraus et al. | |
| 6,355,239 B1 | 3/2002 | Bruder et al. | |
| 6,368,636 B1 | 4/2002 | McIntosh et al. | |
| 6,387,367 B1 | 5/2002 | Davis-Sproul et al. | |
| 6,387,369 B1 | 5/2002 | Pittenger et al. | |
| 6,497,875 B1 | 12/2002 | Sorrell et al. | |
| 6,541,024 B1 | 4/2003 | Kadiyala et al. | |
| 6,548,299 B1 * | 4/2003 | Pykett et al. ............... 435/377 |
| 6,685,936 B2 | 2/2004 | McIntosh et al. | |
| 6,709,864 B1 | 3/2004 | Pittenger et al. | |
| 6,753,181 B2 * | 6/2004 | Atala ......................... 435/376 |
| 6,797,269 B2 | 9/2004 | Mosca et al. | |
| 6,800,480 B1 * | 10/2004 | Bodnar et al. ............. 435/325 |
| 6,835,377 B2 | 12/2004 | Goldberg et al. | |
| 6,863,900 B2 | 3/2005 | Kadiyala et al. | |
| 6,875,430 B2 | 4/2005 | McIntosh et al. | |
| 7,029,666 B2 | 4/2006 | Bruder et al. | |
| 2001/0005591 A1 | 6/2001 | Qasba et al. | |
| 2002/0123141 A1 | 9/2002 | Hariri | |
| 2003/0044977 A1 | 3/2003 | Sakuragawa et al. | |
| 2003/0109042 A1 * | 6/2003 | Wu et al. .................... 435/372 |
| 2003/0161818 A1 | 8/2003 | Weiss et al. | |
| 2003/0180269 A1 | 9/2003 | Hariri | |
| 2003/0235563 A1 | 12/2003 | Strom et al. | |

(Continued)

FOREIGN PATENT DOCUMENTS

CN 1548529 5/2003

(Continued)

OTHER PUBLICATIONS

Pera et al, J Cell Sci 2000;113:5-10.*

(Continued)

*Primary Examiner*—Q. Janice Li
(74) *Attorney, Agent, or Firm*—Jones Day

(57) ABSTRACT

A method of manufacturing a tissue matrix for implantation into a patient is disclosed. The method sets forth collecting embryonic stem cells from a placenta which has been treated to remove residual cord blood and seeding the collected stem cells onto or into a tissue matrix. The seeded tissue matrix is then implanted on or into a patient. The seeded tissue matrix made by the method of the present invention is also disclosed.

5 Claims, 8 Drawing Sheets

U.S. PATENT DOCUMENTS

| | | |
|---|---|---|
| 2003/0235909 A1 | 12/2003 | Hariri |
| 2004/0018617 A1 | 1/2004 | Hwang |
| 2004/0028660 A1 | 2/2004 | Hariri |
| 2004/0048372 A1 | 3/2004 | Hariri |
| 2004/0048796 A1 | 3/2004 | Hariri |
| 2004/0107453 A1 | 6/2004 | Furcht et al. |
| 2004/0136967 A1 | 7/2004 | Weiss et al. |
| 2004/0161419 A1 | 8/2004 | Strom et al. |
| 2004/0171147 A1 | 9/2004 | Hariri |
| 2004/0180040 A1 | 9/2004 | Phillips, et al. |
| 2004/0219136 A1 | 11/2004 | Hariri |
| 2004/0229351 A1 | 11/2004 | Rodriguez et al. |
| 2005/0019865 A1 | 1/2005 | Kihm et al. |
| 2005/0019908 A1 | 1/2005 | Hariri |
| 2005/0032209 A1 | 2/2005 | Messina et al. |
| 2005/0037491 A1 | 2/2005 | Mistry et al. |
| 2005/0042595 A1 | 2/2005 | Haas |
| 2005/0054093 A1 | 3/2005 | Haas |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Khim et al. |
| 2005/0085543 A1 | 4/2005 | Wallimann et al. |
| 2005/0089513 A1 | 4/2005 | Sakuragawa et al. |
| 2005/0112104 A1 | 5/2005 | Pittenger et al. |
| 2005/0118715 A1 | 6/2005 | Hariri |
| 2005/0124003 A1 | 6/2005 | Atala et al. |
| 2005/0143420 A1 | 6/2005 | Moutouh-de Parseval |
| 2005/0148034 A1 | 7/2005 | Payvandi |
| 2005/0148074 A1 | 7/2005 | Davies et al. |
| 2005/0176139 A1 | 8/2005 | Chen et al. |
| 2005/0181502 A1 | 8/2005 | Furcht et al. |
| 2005/0186182 A1 | 8/2005 | Deisher et al. |
| 2005/0233452 A1 | 10/2005 | Ho et al. |
| 2005/0239897 A1 | 10/2005 | Pittenger et al. |
| 2005/0276792 A1 | 12/2005 | Kaminski |
| 2005/0283844 A1 | 12/2005 | Furcht et al. |
| 2006/0008450 A1 | 1/2006 | Verfaille et al. |
| 2006/0078993 A1 | 4/2006 | Phan et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0222634 A1 | 10/2006 | Clarke et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2006/0263337 A1 | 11/2006 | Maziarz et al. |
| 2006/0281178 A1 | 12/2006 | Sakuragaw et al. |

FOREIGN PATENT DOCUMENTS

| | | |
|---|---|---|
| EP | 1288293 A1 | 3/2003 |
| EP | 1384775 A1 | 1/2004 |
| EP | 1535994 A1 | 6/2005 |
| JP | 2003235549 | 12/2002 |
| JP | 2005151907 | 11/2003 |
| WO | WO 91/06666 | 5/1991 |
| WO | WO 98/37903 | 9/1998 |
| WO | WO99/64566 A3 | 12/1999 |
| WO | WO00/17325 A1 | 3/2000 |
| WO | WO00/27999 A3 | 5/2000 |
| WO | WO 00/73421 | 12/2000 |
| WO | WO 03/042405 | 5/2003 |
| WO | WO03/089619 | 10/2003 |
| WO | WO2004/087896 | 10/2004 |
| WO | WO2005042703 | 5/2005 |
| WO | WO2005105992 | 11/2005 |
| WO | WO2006/015214 | 2/2006 |

OTHER PUBLICATIONS

Thomson et al, Science 1998;282:1145-7.*
Donovan and Gearhart, Nat Nov. 2001;414:92-97.*
Buttery et al, Tissue Eng Feb. 2001;7:89-99.*
Lorkowski et al, Pure Appl Chem 2002;74:2057-81.*
Huss et al, J Hematother Stem Cell Res Dec. 2000;9(6):783-93.*
Hadjantonakis, A.-K, et al; "The Stem Cells of Early Embryos." *Differentiation*, vol. 68, pp. 159-166, Oct. 2001.
Rossant, J.; "Stem Cells from the Mammalian Blastocyst". *Stem Cells*, vol. 19, pp. 477-482, Nov. 2001.
Vacanti, J.P., et al. "Selective Cell Transplantation Using Bioabsorbable Artifical Polymers as Matrices", *J. Pediatric Surg*, vol. 23, p. 3 (1988).
Moore et al. "A simple perfusion technique for the isolation of maternal intervillous blood mononuclear cells from human placentae," *J. Immunological Meths.* 209(1):93-104 (1997).
Contractor, et al., "A comparison of the effects of different perfusion regimes on the structure of the isolated human placental lobule," *Cell and Tissue Res.* 237(3):609-617 , (1984).
Abkowitz, "Can Human Hematopoietic Stem Cells Become Skin, Gut, or Liver Cells?" N. Engl. J. Med. 346(10):770-2 (2002).
Chin et al., "Enhanced Interferon Production and Lymphokine-Activated Cytotoxicity of Human Placental Cells," *Cellular Immunology* 113:1-9 (1988).
Chao, et al., "Stem Cell Transplantation (Cord Blood Transplants)." American Society of Hematololgy, Hematology 2004, p. 354-71.
Cosma, et al., "Use and Application of Stem Cells in Toxicology." SOT 2003 Annual Meeting, p. 4, Abstract 19.
Davila, et al., "Use and Application of Stem Cells in Toxicology." Toxicological Sciences 79, 214-223 (2004).
De Coppi, et al., "Amniotic Fluid and Chorionic Villi Derived Human Stem Cells for the Engineering of Tissues in Vivo." The Journal of Urology, vol. 171, No. 4, Supplement, Saturday, May 8, 2004, p. 21, Abstract 81.
De Coppi, et al., "Human Embryonic and Fetal Stem-Cell Isolation from Amniotic Fluid and Placenta for Tissue Reconstruction." Urology and Reproductive Surgery, vol. 195, No. 3S, Sep. 2002, p. S93.
De Coppi et al., "Human fetal stem cell isolation from amniotic fluid for tissue reconstruction," *J. Urology* 167(4 Supp.) 85 (Abstract 338) (2002).
De Coppi, et al., "Pluripotent Stem Cells Derived from Human Chorionic Villi and Amniotic Fluid for Tissue Engineering Applications." Experimental Biology/IUPS 2005: Meeting Abstracts, A1366, Abstract 781.7.
De Filippo, et al., "Total Penile Urethra Replacement with Autologous Cell-Seeded Collagen Matrices." Urology and Reproductive Surgery, vol. 195, No. 3S, Sep. 2002, p. S95.
Dushnik-Levinson, et al., "Embryogenesis in Vitro: Study of Differentiation of Embryonic Stem Cells." Biol. Neonate. 67(2):77-83.
Hatzopoulos, et al., "Isolation and Characterization of Endothelial Progenitor Cells from Mouse Embryos." Development. 125(8):1457-68 (1998).
Himori, et al. Chemotherapeutic Susceptibility of Human Bone Marrow Progenitor Cells and Human Myelogenous Leukemia Cells (HL-60) in Co-Culture: Preliminary Report. Int. J. Cell Cloning. 2(4):254-62 (1984).
Hirashima, et al., "Maturation of Embryonic Stem Cells into Endothelial Cells in an In Vitro model of Vasculogenesis." Blood. 93(4):1253-63 (1999).
Koh, et al., "Parthenolgenetically Derived Stem Cells for Urologic Reconstruction." The Journal of Urology, vol. 171, No. 4, Supplement, Saturday, May 8, 2004, p. 21, Abstract 81.
Korbling, et al., "Hepatocytes and Epithelial Cells of Donor Origin in Recipients of Peripheral-Blood Stem Cells." N. Engl. J. Med. 346(10):738-46 (2002).
Miki, et al., "Isolation of Multipotent Stem Cells from Placenta." AASLD Abstracts, Hepatology, Oct. 2003, Abstract 279, p. 290A.

Miki, et al., "Production of Hepatocytes from Human Amniotic Stem Cells." HEPATOLOGY, Abstract 20, vol. 36, No. 4, Pt. 2, 2002.

Miki, et al., "Stem Cell Characteristics of Amniotic Epithelial Cells." Stem Cells Express, published online Aug. 9, 2005; doi:10.1634/stemcells.2004-0357.

Reyes, et al., "Origin of Endothelial Progenitors in Human Postnatal Bone Marrow." J. Clin. Invest. 109(3):337-46.

Sakuragawa et al., "Expression of markers for both neuronal and glial cells in human amniotic epithelial cells," *Neuroscience Letters* 209:9-12 (1996).

Sakuragawa et al., "Human amniotic epithelial cells are promising transgene carriers for allogeneic cell transplantation into liver," *J. Hum. Genet*. 45:171-176 (2000).

Shamblott, et al., "Derivation of Pluripotent Stem Cells from Cultured Human Primordial Germ Cells." Proc. Nat'l. Acd. Sci. U S A. 95(23):13726-31 (1998).

Slager, "Transforming Growth Factor-Beta in the Early Mouse Embryo: Implications for the Regulation of Muscle Formation and Implantation." Dev. Genet. 14(3):212-24 (1993).

ScienCell—Human Amniotic Epithelial Cells. http://www.sciencellonline.com/products/7100.htm.

Thomson, et al., "Embryonic Stem Cell Lines Derived from Human Blastocysts." Science 282(5391):1145-47 (1998).

U.S. Appl. No. 11/580,588, filed Oct. 13, 2006, Paludan.
U.S. Appl. No. 11/580,625, filed Oct. 13, 2006, Heidaran.
U.S. Appl. No. 11/648,802, filed Dec. 28, 2006, Heidaran.
U.S. Appl. No. 11/648,804, filed Dec. 28, 2006, Edinger.
U.S. Appl. No. 11/648,812, filed Dec. 28, 2006, Heidaran.
U.S. Appl. No. 11/648,813, filed Dec. 28, 2006, Edinger.
U.S. Appl. No. 11/648,824, filed Dec. 28, 2006, Heidaran.

* cited by examiner

Drained, Perfused Placenta Stored in Air-Tight Container

TISSUE MATRICES COMPRISING PLACENTAL STEM CELLS, AND METHODS OF MAKING THE SAME

BENEFIT OF PRIOR PROVISIONAL APPLICATION

This utility patent application claims the benefit of co-pending prior U.S. Provisional Patent Application Ser. No. 60/268,560, filed Feb. 14, 2001, entitled "Renovation and Repopulation of Decellularized Cadaveric Organs by Stem Cells" having the same named applicant as inventor, namely Robert J. Hariri.

BACKGROUND OF THE INVENTION

1. Field of the Invention

The present invention is generally in the field of tissue engineering, and more specifically is a means for obtaining stem cells for seeding onto scaffolding for regeneration or repair of tissue, bone and other organs.

2. Description of the Background Art

The scarcity of human donor organs for transplantation is a growing problem. Despite aggressive public awareness campaigns the numbers of qualified organ donors has changed little in the last 20 years while the demand has grown at a rapid pace. In addition, allogeneic organ transplantation is still associated with a high frequency of complications due to immune rejection. Attempts to address this crisis have included development of ex vivo and implantable synthetic organ support devices such as pump devices for cardiac support and use of organs from other species (xenotransplantation). Xenotransplantation has been refined to include development of chimeric donor animals yet is still unperfected and subject to possible consequences such as the transmission of zoonoses.

Human stem cells are totipotential or pluripotential precursor cells capable of generating a variety of mature human cell lineages. This ability serves as the basis for the cellular differentiation and specialization necessary for organ and tissue development. Recent success at transplanting such stem cells have provided new clinical tools to reconstitute and/or supplement the bone marrow after myeloablation due to disease, exposure to toxic chemical or radiation. Further evidence exists which demonstrates that stem cells can be employed to repopulate many, if not all, tissues and restore physiologic and anatomic functionality. Evidence to date indicates that multipotent or pluripotent stem cells are directed to differentiate into specific mature cell lineages based on the physical and biochemical environment that they are delivered. There is also evidence that these cells can migrate from normal to abnormal or defective tissues and repopulate those areas in a very focused and specific manner.

The application of stem cells in tissue engineering, gene therapy and cell therapeutics is also advancing rapidly.

Many different types of mammalian stem cells have been characterized. For example, embryonic stem cells, embryonic germ cells, adult stem cells or other committed stem cells or progenitor cells are known. Certain stem cells have not only been isolated and characterized but have also been cultured under conditions to allow differentiation to a limited extent.

Despite considerable advances made in controlling differentiation of stem cells into mature cells and tissues, actual development of the complex architecture of solid organs has not been accomplished. Tissue engineering has therefore directed attention at growing component tissues and then assembling those components into useful structures.

It is therefore an object of the present invention to provide methods to remove the cellular content of tissues while preserving the extracellular matrix architecture coupled with advanced understanding of stem cells, which can be seeded with cells to yield whole organs with the anatomic and physiologic features of native organs.

SUMMARY OF THE INVENTION

Cadaveric solid organs are processed to remove all living cellular components yet preserve the underlying extracellular matrix scaffold in preparation for the implantation of allogeneic stem cells which repopulate the three-dimensional organ scaffold and restore normal anatomic and physiologic function for the purpose of organ transplantation. In a preferred embodiment, the cells are obtained from placental tissue. The method for the processing of cadaveric solid organs selectively depletes the cellular components of the organ while preserving the native biochemical and 3-dimensional architecture of said organ. The resulting organ scaffold or 'template' is then implanted with genotype-specific, living multi-potent stem cells which are delivered by intraparenchymal injection or through the organ's vascular tree. Delivery of these cells is made in a manner that promotes the differentiation and proliferation of the normal mature cell types of the organ, the distribution and ultimate cell to cell assembly being guided by the extracellular matrix scaffold. The repopulation of the organ scaffold takes place under environmentally-controlled culture conditions providing immersion in and perfusion with tissue culture media formulated to deliver the optimal nutrient and metabolic levels necessary to sustain the organ, while simulating those biomechanical forces found in vivo. The system monitors the physiologic and metabolic state of the organ during repopulation and renovation and adjusts conditions as needed to maintain the optimal steady state. Repopulated organs can then be maintained under these support conditions until such time that they can be tested and transplanted.

The present invention relates to methods of manufacturing a tissue or organ in vivo. The methods of the invention encompass using embryonic-like stem cells obtained from a placenta which has been treated to remove residual cord blood to seed a matrix and cultured under the appropriate conditions to allow the stem cells to differentiate and populate the matrix. The tissues and organs obtained by the methods of the invention may be used for a variety of purposes, including research and therapeutic purposes.

In accordance with the present invention, embryonic-like stem cells are obtained from a placenta which has been exsanguinated and perfused for a period of at least two to twenty four hours following expulsion from the uterus to remove all residual cells. The exsanguinated placenta is then cultured under the appropriate conditions to allow for the production of endogenous stem cells originating from the placenta.

The methods of the present invention relate to the use of embryonic-like stem cells which have been originated from a placenta to seed a matrix. Once obtained from a cultured placenta, the embryonic-like stem cells may be characterized by a number of methods, including but not limited to, immunochemistry, and the presence of particular cell surface markers. Preferred stem cells to be used in accordance with the present invention may be identified by the presence of the following cell surface markers: CD10+, CD29+, CD34−, CD44+, CD45−, CD54+, CD90+, SH2+, SH3+, SH4+, SSEA3−, SSEA4−, OCT-4+, and APC-p+.

In accordance with the methods of the present invention, the stem cells may be differentiated along specific cell lineages, including adipogenic, chondrogenic, osteogenic, neurogenic and hepatogenic lineages. In another embodiment of the invention, it may be preferable to stimulate differentiation of embryonic-like stem cells to a particular lineage prior to seeding the cells to a particular matrix. In accordance with this embodiment, cultured placentas may be stimulated to produce cells of a particular lineage, by introducing into the placenta exogenous cells or tissues of the desired lineage. For example, prior to seeding embryonic-like stem cells on a matrix or decellularized organ for propagation and growth into liver tissue, the cultured placenta may be stimulated to produce hepatogenic stem cells by introducing exogenous hepatogenic cells or tissue into the placenta.

The present invention also relates to the use of the cultured placenta as a bioreactor to stimulate the propagation of embryonic-like stem cells of a particular lineage. For example, the cultured placenta can be stimulated to produce embryonic-like stem cells which have become committed to a particular lineage, including but not limited to, adipogenic, chondrogenic, osteogenic, neurogenic and hapatogic lineages. In accordance with this embodiment of the invention, the cultured placenta may be stimulated to produce cells of a particular lineage, by exposing the cultured placenta to exogenous cells or tissues of the desired lineage.

By way of example, and not by way of limitation, in order to generate cells of a hepatic lineage, the placenta may be exposed to liver cells. In accordance with this embodiment, liver cells are introduced into the placenta by any number of methods, including injecting the liver cells as a single cell suspension or as islands of cells into the vasculature or directly into the placenta. Following introduction of the liver cells, the placenta would be perfused in accordance with the methods described herein to allow for the recovery of hepatic stem cells from the placenta.

DETAILED DESCRIPTION OF THE INVENTION

Figure 1:
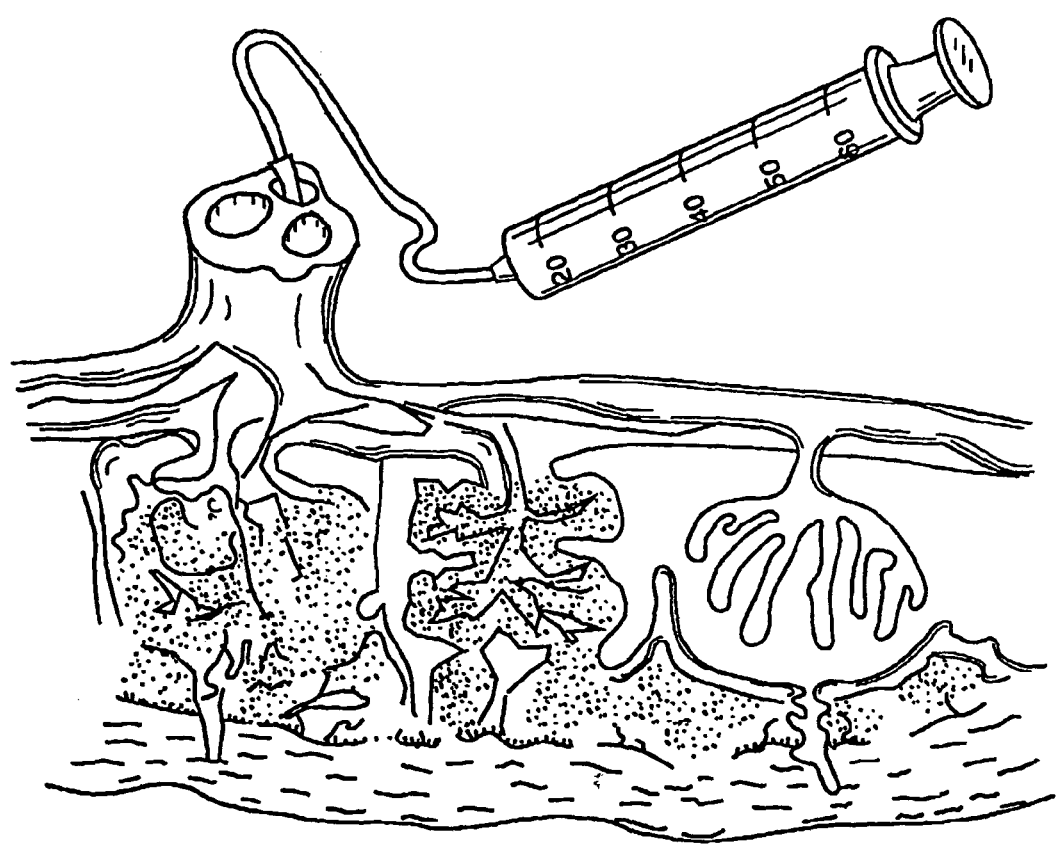
FIG. 1 is a cross-sectional view of the cannulation of the vein and artery of a placenta to perfuse the placenta and then collect the perfusate.
Figure 2A:
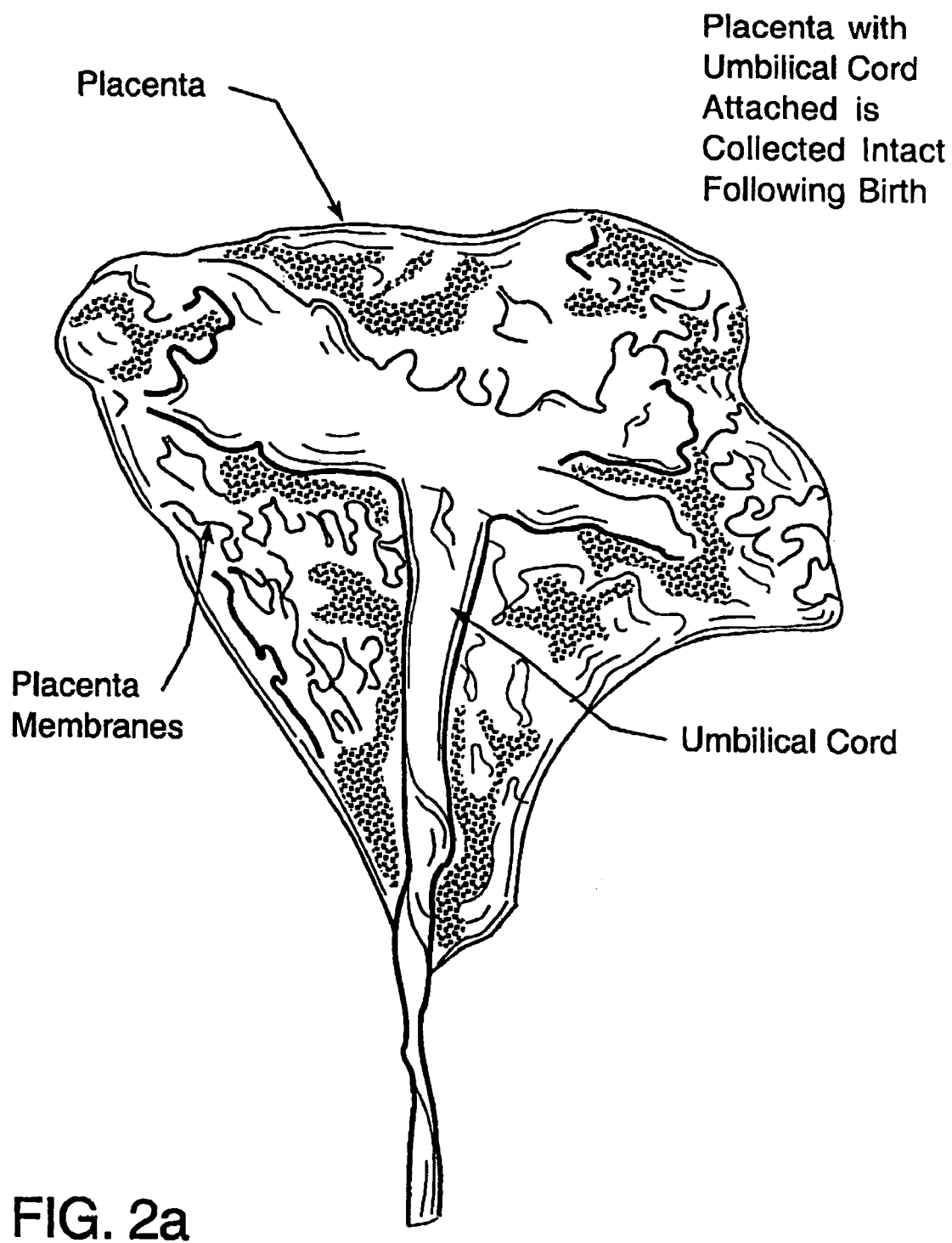
FIGS. 2a-e are schematics showing the collection, clamping, perfusion, collection and storage of a drained and perfused placenta.
Figure 2B:
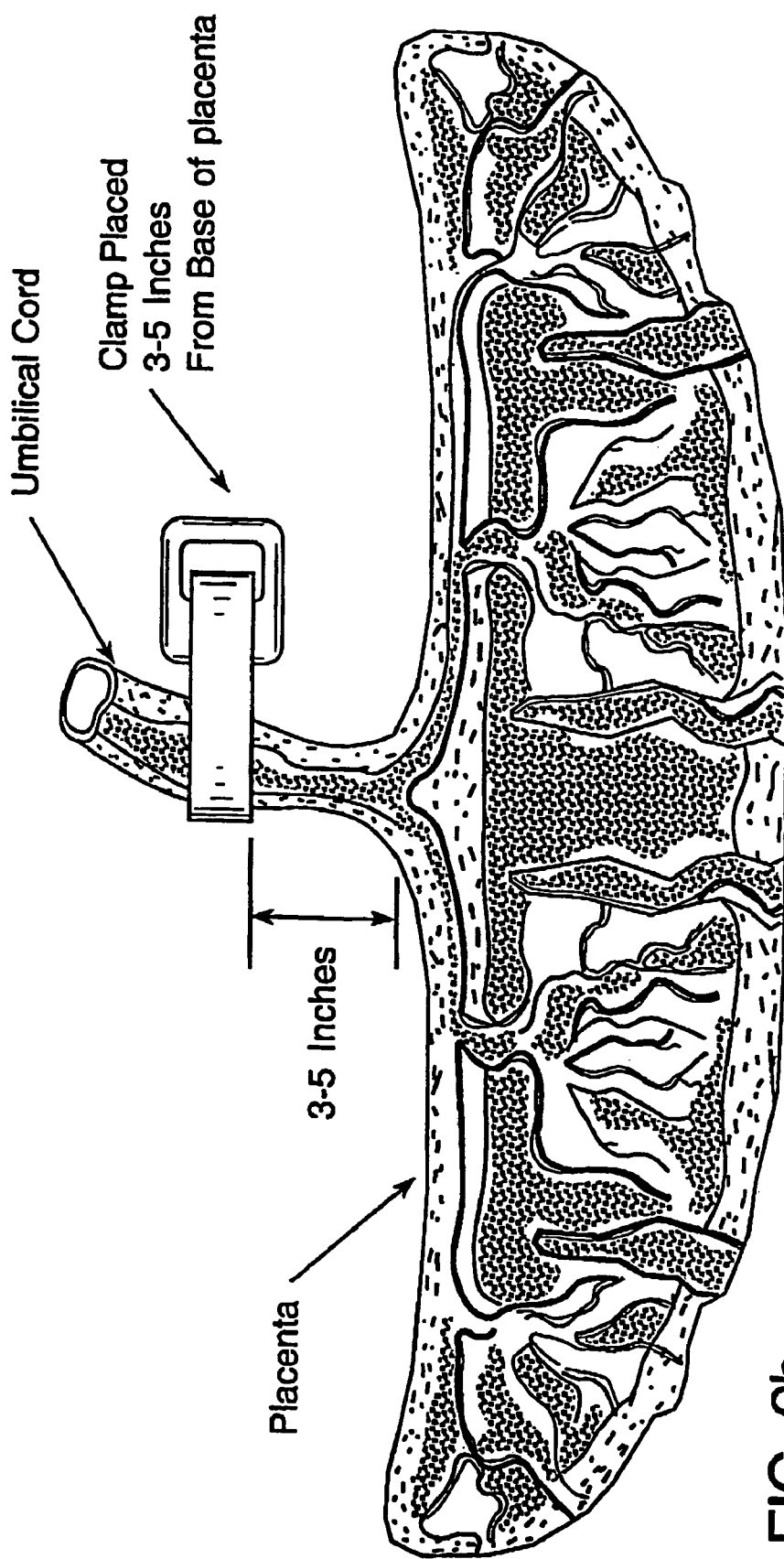
Figure 2C:
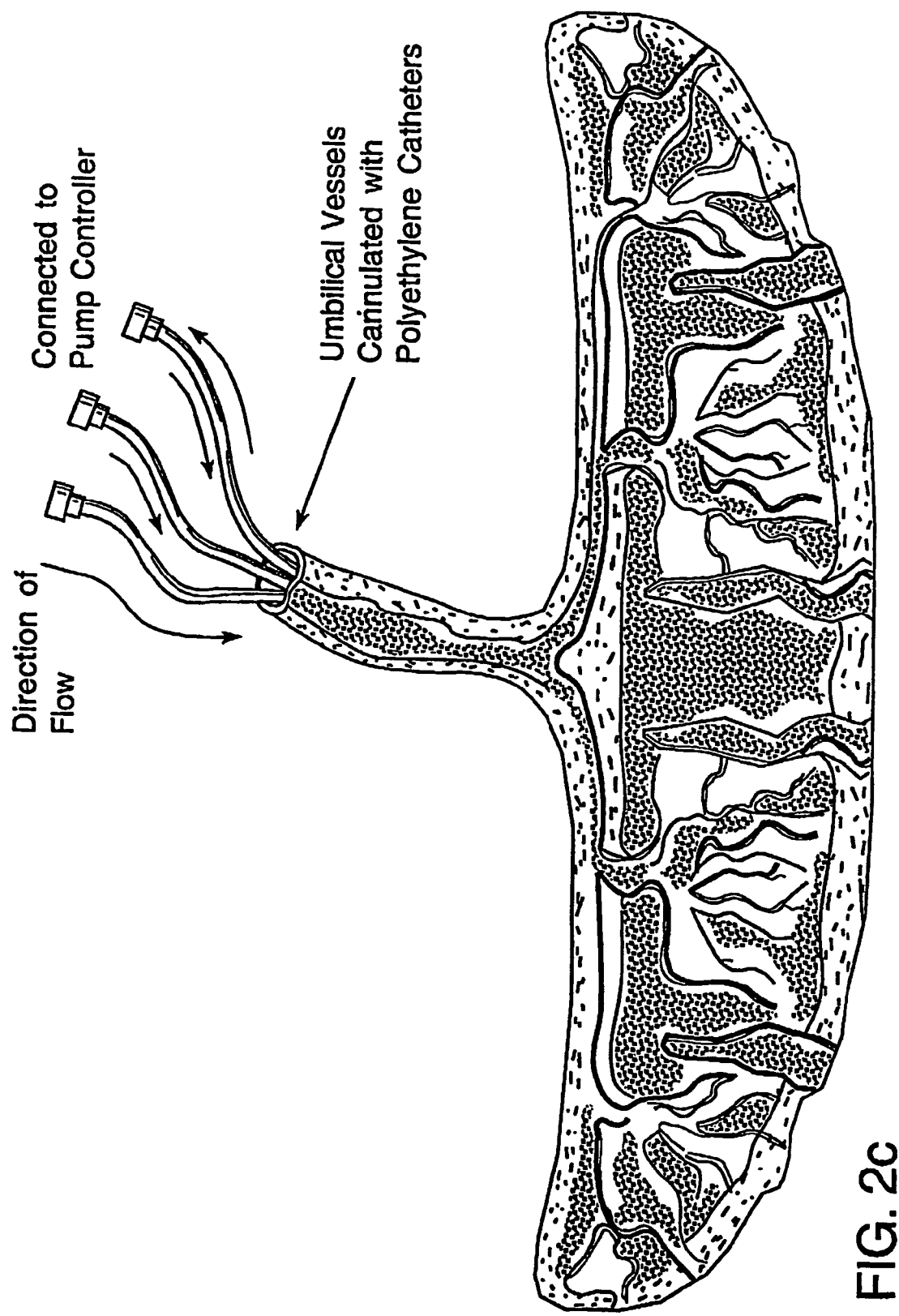
Figure 2D:
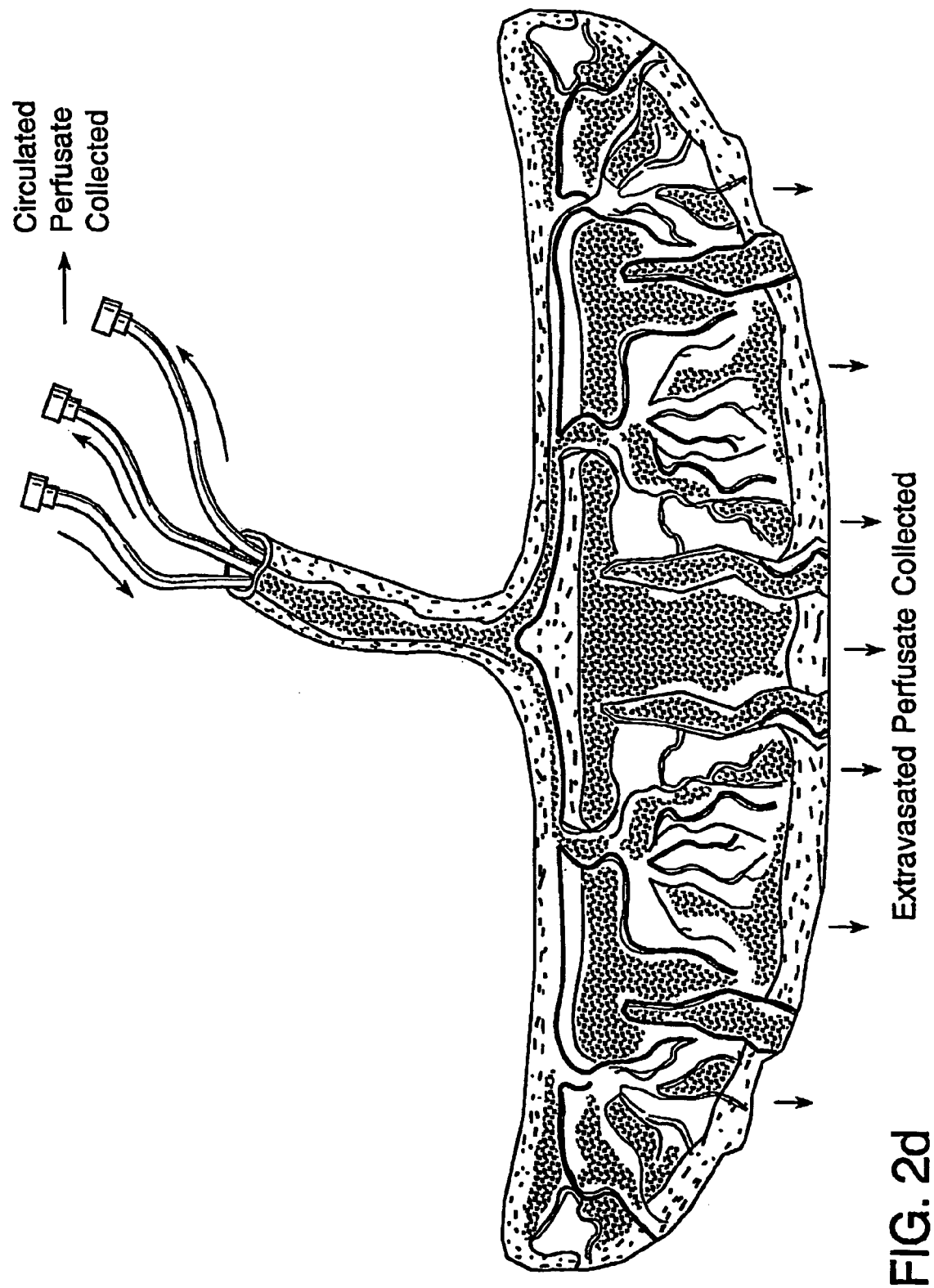
Figure 2E:
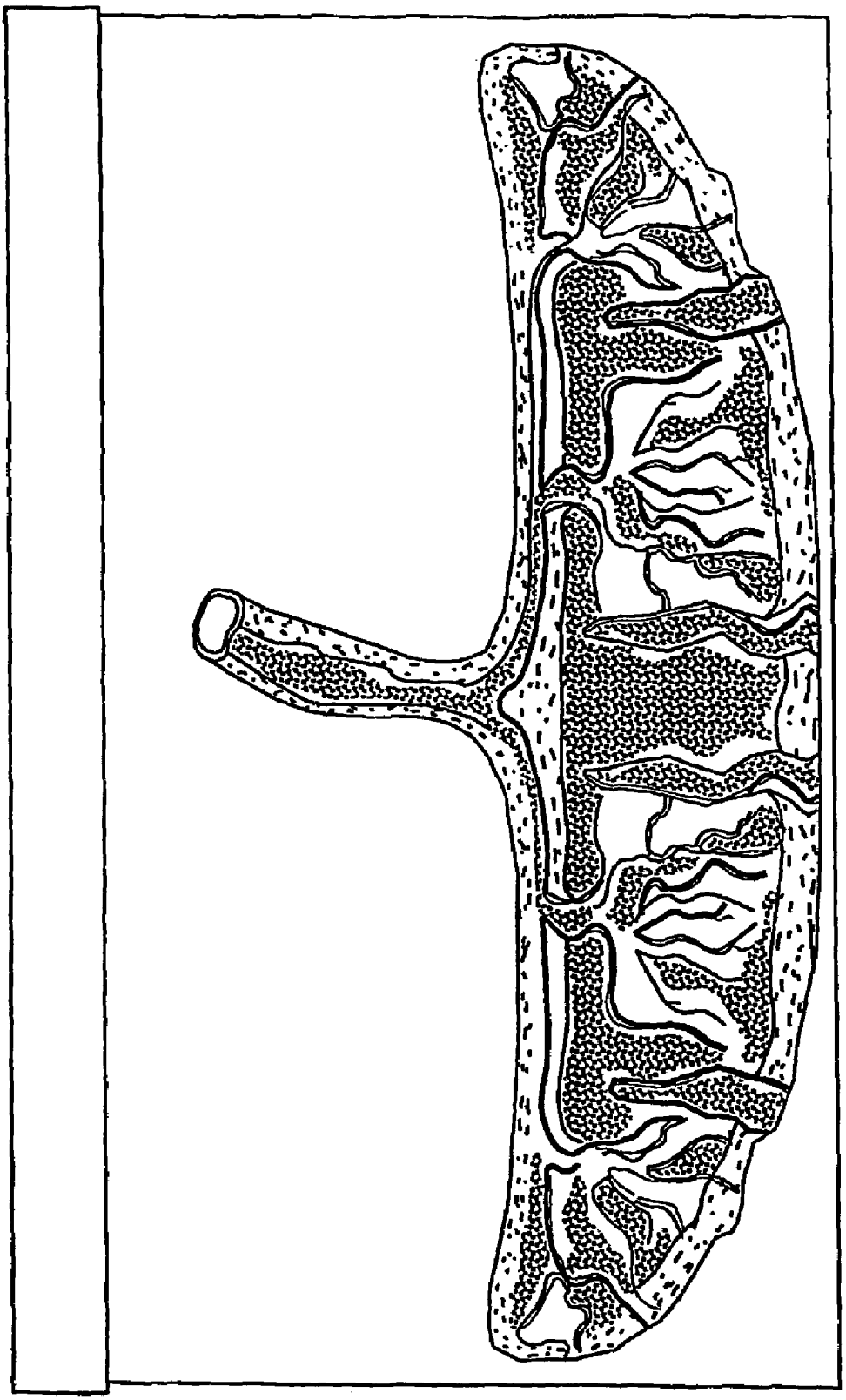

As used herein, the term "bioreactor" refers to an ex vivo system for propagating cells, producing or expressing biological materials and growing or culturing cells, tissues, organoids, viruses and microorganisms.

As used herein, the term "embryonic stem cell" refers to a cell that is derived from the inner cell mass of a blastocyst (e.g., a 4- to 5-day-old human embryo) and that is pluripotent.

As used herein, the term "embryonic-like stem cell" refers to a cell that is not derived from the inner cell mass of a blastocyst. As used herein, an "embryonic-like stem cell" may also be referred to as a "placental stem cell." An embryonic-like stem cell, however, may be a pluripotent cell, a multipotent cell, or a committed progenitor cell. According to the methods of the invention, embryonic-like stem cells derived from the placenta may be collected from the isolated placenta once it has been exsanguinated and perfused for a period of time sufficient to remove residual cells.

As used herein, the term "exsanguinated" or "exsanguination," when used with respect to the placenta, refers to the removal and/or draining of substantially all cord blood from the placenta. In accordance with the present invention, exsanguination of the placenta can be achieved by, for example, but not by way of limitation, draining, gravity induced efflux, massaging, squeezing, pumping, etc. Exsanguination of the placenta may further be achieved by perfusing, rinsing or flushing the placenta with a fluid that may or may not contain agents, such as anticoagulants, to aid in the exsanguination of the placenta.

As used herein, the term "perfuse" or "perfusion" refers to the act of pouring or passaging a fluid over or through an organ or tissue, preferably the passage of fluid through an organ or tissue with sufficient force or pressure to remove any residual cells, e.g., non-attached cells from the organ or tissue. As used herein, the term "perfusate" refers to the fluid collected following its passage through an organ or tissue.

As used herein, the term "exogenous cell" refers to a "foreign" cell, i.e., a heterologous cell (i.e., a "non-self" cell derived from a source other than the placental donor) or autologous cell (i.e., a "self" cell derived from the placental donor) that is derived from an organ or tissue other than the placenta.

As used herein, the term "organoid" refers to an aggregation of one or more cell types assembled in superficial appearance or in actual structure as any organ or gland of a mammalian body, preferably the human body.

As used herein, the term "multipotent cell" refers to a cell that has the capacity to grow into any of subset of the mammalian body's approximately 260 cell types. Unlike a pluripotent cell, a multipotent cell does not have the capacity to form all of the cell types.

As used herein, the term "pluripotent cell" refers to a cell that has complete differentiation versatility, i.e., the capacity to grow into any of the mammalian body's approximately 260 cell types. A pluripotent cell can be self-renewing, and can remain dormant or quiescent within a tissue. Unlike a totipotent cell (e.g., a fertilized, diploid egg cell), an embryonic stem cell cannot usually form a new blastocyst.

As used herein, the term "progenitor cell" refers to a cell that is committed to differentiate into a specific type of cell or to form a specific type of tissue.

As used herein, the term "stem cell" refers to a master cell that can reproduce indefinitely to form the specialized cells of tissues and organs. A stem cell is a developmentally pluripotent or multipotent cell. A stem cell can divide to produce two daughter stem cells, or one daughter stem cell and one progenitor ("transit") cell, which then proliferates into the tissue's mature, fully formed cells.

As used herein, the term "totipotent cell" refers to a cell that is able to form a complete embryo (e.g., a blastocyst).

I. Tissue Matrices

Decellularized Tissue Matrices

A xenogeneic (or allogeneic) tissue matrix is processed to remove native cells and other antigens and cellular debris from the decellularized tissue matrix, and, optionally, treated to inhibit generation of new immunological sites. Optionally, this tissue matrix can then be treated with the cellular adhesion factors described below to enhance attachment of cells to the matrix during the process of repopulating the tissue matrix with such new cells. Different properties of the resulting matrix can be obtained through the selection of cell types used to repopulate the natural tissue matrices, such as the ability to synthesize proteins otherwise atypical for the natural tissue at the site of implantation or unique to certain age groups. These hybrid grafts combine the structural advantages of bioprosthetic grafts with the functional and regenerative capabilities of allografts as well as display attenuated or no immune response, limited propensity to calcify, and little stimulation of thromboembolism.

Depending on the type of transplant intended, if the recipient is human, the initial transplant tissue or organ may be of non-human origin. These tissues or organs may be obtained at approved slaughterhouses from animals fit for human consumption or from herds of domesticated animals maintained for the purpose of providing these tissues or organs. The tissues or organs are handled in a sterile manner, and any further dissection of the tissue or organs is carried out under aseptic conditions.

After collection and dissection, this tissue may be sterilized by incubating it in a sterile buffered nutrient solution containing antimicrobial agents, for example an antibacterial, an antifungal, or a sterilant compatible with the transplant tissue. The sterilized transplant tissue may then be cryopreserved for further processing at a later time or may immediately be further processed according to the next steps of this process including a later cryopreservation of the tissue matrix or other tissue products of the process.

The tissue is first decellularized. Native viable cells as well as other cellular and acellular structures or components which may elicit an adverse immune response by the implant recipient are removed. Several means of reducing the viability of native cells in tissues and organs are known, including physical, chemical, and biochemical methods. See, e.g. U.S. Pat. No. 5,192,312 (Orton) which is incorporated herein by reference. Such methods may be employed in accordance with the process described herein. However, the decellularization technique employed should not result in gross disruption of the anatomy of the transplant tissue or substantially alter the biomechanical properties of its structural elements. The treatment of the tissue to produce a decellularized tissue matrix should also not leave a cytotoxic environment that mitigates against subsequent repopulation of the matrix with cells that are allogeneic or autologous to the recipient. Cells and tissues that are allogeneic to the recipient are those that originate with or are derived from a donor of the same species as the recipient. Autologous cells or tissues are those that originate with or are derived from the recipient.

Physical forces, for example the formation of intracellular ice, can be used to decellularize transplant tissues. For example, vapor phase freezing (slow rate of temperature decline) of intact heart valves can reduce the cellularity of the heart valve leaflets as compared to liquid phase freezing (rapid). However, slow freezing processes, in the absence of cryoprotectant, may result in tissue disruption such as the cracking of heart valve conduits. Colloid-forming materials may be added during freeze-thaw cycles to alter ice formation patterns in the tissue. Polyvinylpyrrolidone (10% w/v) and dialyzed hydroxyethyl starch (10% w/v) may be added to standard cryopreservation solutions (DMEM, 10% DMSO, 10% fetal bovine serum) to reduce extracellular ice formation while permitting formation of intracellular ice. This allows a measure of decellularization while providing the tissue matrix with some protection from ice damage.

Alternatively, various enzymatic or other chemical treatments to eliminate viable native cells from implant tissues or organs may be used. For instance, extended exposure of cells to proteases such as trypsin result in cell death. However, because at least a portion of the type I collagen molecule is sensitive to a variety of proteases, including trypsin, this may not be the approach of choice for collagenous grafts intended for implant in high mechanical stress locations.

Combinations of different classes of detergents, for example, a nonionic detergent, Triton X-100, and an anionic detergent, sodium dodecyl sulfate, may disrupt cell membranes and aid in the removal of cellular debris from tissue. However, steps should be taken to eliminate any residual detergent levels in the tissue matrix, so as to avoid interference with the later repopulating of the tissue matrix with viable cells.

The decellularization of the transplant tissue is preferably accomplished by the administration of a solution effective to lyse native cells in the transplant tissue. Preferably, the solution is an aqueous hypotonic or low ionic strength solution formulated to effectively lyse the native tissue cells. Such an aqueous hypotonic solution may be de-ionized water or an aqueous hypotonic buffer. Preferably the aqueous hypotonic buffer may contain additives that provide suboptimal conditions for the activity of selected proteases, for example collagenase, which may be released as a result of cellular lysis. Additives such as metal ion chelators, for example 1,10-phenanthroline and ethylenediaminetetraacetic acid (EDTA), create an environment unfavorable to many proteolytic enzymes. Providing sub-optimal conditions for proteases such as collagenase, may assist in protecting the tissue matrix from degradation during the lysis step. Sub-optimal conditions for proteases may be achieved by formulating the hypotonic lysis solution to eliminate or limit the amount of calcium and zinc ions available in solution. Many proteases are active in the presence of calcium and zinc ions and lose much of their activity in calcium and zinc ion free environments. Preferably, the hypotonic lysis solution will be prepared selecting conditions of pH, reduced availability of calcium and zinc ions, presence of metal ion chelators and the use of proteolytic inhibitors specific for collagenase such that the solution will optimally lyse the native cells while protecting the underlying tissue matrix from adverse proteolytic degradation. For example a hypotonic lysis solution may include a buffered solution of water, pH 5.5 to 8, preferably pH 7 to 8, free from calcium and zinc ions and including a metal ion chelator such as EDTA. Additionally, control of the temperature and time parameters during the treatment of the tissue matrix with the hypotonic lysis solution, may also be employed to limit the activity of proteases.

It is preferred that the decellularization treatment of the tissue matrix also limits the generation of new immunological sites. While collagen is typically substantially non immunogenic, partial enzymatic degradation of collagen may lead to heightened immunogenicity. Accordingly, a preferable step of this process includes treatment of the tissue with enzymes, such as nucleases, effective to inhibit cellular metabolism, protein production and cell division without degrading the underlying collagen matrix. Nucleases that can be used for digestion of native cell DNA and RNA include both exonucleases and endonucleases. A wide variety of which are suitable for use in this step of the process and are commercially available. For example, exonucleases that effectively inhibit cellular activity include DNAase I (SIGMA Chemical Company, St. Louis, Mo.) and RNAase A (SIGMA Chemical Company, St. Louis, Mo.) and endonucleases that effectively inhibit cellular activity include EcoR I (SIGMA Chemical Company, St. Louis, Mo.) and Hind III (SIGMA Chemical Company, St. Louis, Mo.).

It is preferable that the selected nucleases are applied in a physiological buffer solution which contains ions which are optimal for the activity of the nuclease. Such ions include magnesium and calcium salts. It is also preferred that the ionic concentration of the buffered solution, the treatment temperature and the length of treatment are selected to assure the desired level of effective nuclease activity. The buffer is preferably hypotonic to promote access of the nucleases to tile cell interiors. For treatment of endogenous endothelial cells of non-human heart valve tissue, particularly valves of porcine or bovine origin the tissue is preferably treated with a physiologically buffered medium comprised of nucleases DNAase I and RNAase A. Preferably, the nuclease degradation solution contains about 0.1 microgram/ml to 50 microgram/ml, preferably 10 microgram/ml, of the nuclease DNAase I, and 0.1 microgram/ml to 10 microgram/ml, preferably 1.0 microgram/ml, of RNAase A. The tissue may be decellularized by application of the foregoing at a temperature of about 20 C to 38 C, preferably at about 37 C (Centigrade), for about 30 minutes to 6 hours, while at the same time the generation of new immunological sites as a result of collagen degradation is limited.

Other enzymatic digestions may be suitable for use herein, for example, enzymes that will disrupt the function of native cells in a transplant tissue may be used. For example, phospholipase, particularly phospholipases A or C, in a buffered solution, may be used to inhibit cellular function by disrupting cellular membranes of endogenous cells. Preferably, the enzyme employed should not have a detrimental effect on the tissue matrix protein. The enzymes suitable for use may also be selected with respect to inhibition of cellular integrity, and also include enzymes which may interfere with cellular protein production. The pH of the vehicle, as well as the composition of the vehicle, will also be adjusted with respect to the pH activity profile of the enzyme chosen for use. Moreover, the temperature applied during application of the enzyme to the tissue should be adjusted in order to optimize enzymatic activity.

Following decellularization, the tissue matrix is washed to assure removal of cell debris which may include cellular protein, cellular lipids, and cellular nucleic acid, as well as any extracellular debris such as extracellular soluble proteins, lipids and proteoglycans. Removal of this cellular and extracellular debris reduces the likelihood of the transplant tissue matrix eliciting an adverse immune response from the recipient upon implant. For example, the tissue may be incubated in a balanced salt solution such as Hanks' Balanced Salt Solution (HBSS). The composition of the balanced salt solution wash, and the conditions under which it is applied to the transplant tissue matrix may be selected to diminish or eliminate the activity of the nuclease or other enzyme utilized during the decellularization process. Such a balanced salt wash solution would preferably not contain magnesium or calcium salts, and the washing process may include incubation at a temperature of between about 2 C and 42 C, with 4 C most preferable. The transplant tissue matrix may be incubated in the balanced salt wash solution for up to 10 to 12 days, with changes in wash solution every second or third day. Optionally, an antibacterial, an antifungal or a sterilant or a combination thereof, may be included in the balanced salt wash solution to protect the transplant tissue matrix from contamination with environmental pathogens.

The tissue matrix can be preserved by cryopreservation. Techniques of cryopreservation of tissue are well known in the art. Brockbank, K. G. M. Basic Principles of Viable Tissue Preservation. In: Transplantation Techniques and Use of Cryopreserved Allograft Cardiac Valves and Vascular Tissue. D. R. Clarke (ed.), Adams Publishing Group, Ltd., Boston. pp 9-23, discusses cryopreservation of tissues and organs and is hereby incorporated by reference.

The tissue matrix, whether or not having been cryopreserved, may be next treated to enhance the adhesion and inward migration of the allogeneic or autologous cells, in vitro, which will be used to repopulate the transplant tissue.

The extent of attachment is increased by the addition of serum (human or fetal bovine, maximal binding with 1% serum) and by purified fibronectin to the culture medium. Each of the two homologous subunits of fibronectin has two cell recognition regions, the most important of which has the Arg-Gly-Asp (RGD) sequence. A second site, binding glycosaminoglycans, acts synergistically and appears to stabilize the fibronectin-cell interactions mediated by the RGD sequence. Heparin sulfate along with chondroitin sulfate are the two glycosaminoglycans identified on cell surfaces. Heparin sulfate is linked to core proteins (syndecan or hyaluronectin) which can either be integral or membrane spanning. Cellular binding sites for extracellular matrix glycoproteins are called integrins and these mediate tight binding of cells to the adhesion factors. Each adhesion factor appears to have a specialized integrin although a single integrin may bind to several extracellular matrix factors. Fibroblasts, when adherent to intact fibronectin (cell and heparin-binding domains) display a contracted morphology with focal adhesions. Without the heparin binding domain, fibroblasts will spread but fail to develop focal adhesions.

Another method whereby cell attachment to the matrix is enhanced is by incubation of the decellularized tissue matrix in a nutrient solution containing extracellular matrix protein such as fibronectin and a glycosaminoglycan for a period effective for binding of the fibronectin to surfaces of the transplant tissue matrix to be repopulated. Preferred buffers for use with fibronectin/glycosaminoglycan include sodium phosphate/glycerin/bovine serum albumin (Fetal Bovine Serum, BIO-WHITTAKER) and Dulbecco's Modified Eagle's Medium (DMEM), (GIBCO). These buffers typically are used to provide a physiological acceptable pH of about 7.0 to 7.6. The presence of the extracellular matrix proteins establish a surface on the tissue matrix to which the cells that have been chosen to repopulate the matrix attach. The stimulus of the extracellular matrix protein promotes cell repopulation in the graft. A source of fibronectin is from human blood, processed to limit contamination with virus. The preferred glycosaminoglycan is heparin. The concentration of glycoprotein used as the adhesion factor to treat the tissue matrix may range from about 1 to about 100 microgram/ml, with a fibronectin concentration of 10 microgram/ml being preferred. The preferred weight ratio of fibronectin to heparin is about 10 parts fibronectin to about 1 part glycosaminoglycan, e.g. heparin. This is optimal for repopulation of porcine heart valve leaflets, but may range from about 0.1:1 to about 10:0.1 depending on the tissue used.

A variety of substances may be employed to enhance cell chemotaxis, increasing the rate of directional movement along a concentration gradient of the substance in solution. With respect to fibroblast cells, fibroblast growth factor, platelet-derived growth factor, transforming growth factor-.beta., and the substrate-adhesion molecules, fibrillar collagens, Collagen fragments, and fibronectin are chemotactic for fibroblasts. In contrast to cell adhesion, fibroblast migration requires de novo protein synthesis; protein synthesis in normal fibroblastic cells is stimulated by adhesion of cells to fibronectin, so the processes of cell adhesion and cell migration during repopulation are believed to be interrelated.

Synthetic Tissue Matrices

Tissue matrices can also be formed of synthetic or natural materials, such as collagen or polylactide-co-glycolide. A number of these materials are known. For example, a method for forming artificial skin by seeding a fibrous lattice with epidermal cells is described in U.S. Pat. No. 4,485,097 (Bell), which discloses a hydrated collagen lattice that, in combination with contractile agents such as platelets and fibroblasts and cells such as keratinocytes, is used to produce a skin-like substance. U.S. Pat. No. 4,060,081 (Yannas et al.) discloses a multilayer membrane for use as a synthetic skin that is formed from an insoluble modified collagen material that is very slowly degradable in the presence of body fluids and enzymes. U.S. Pat. No. 4,458,678 (Yannas et al.) discloses a process for making a skin-like material wherein a biodegradable fibrous lattice formed from collagen cross-linked with glycosaminoglycan is seeded with epidermal cells.

U.S. Pat. No. 4,520,821 (Schmidt) describes a similar approach to make linings to repair defects in the urinary tract. Epithelial cells are implanted onto the surface of a liquid impermeable synthetic polymeric matrix where they form a monolayer lining on the matrix.

Vacanti, et al., "Selective cell transplantation using bio-absorbable artificial polymers as matrices" *J. Pediat. Surg.* 23, 3-9 (1988) and Vacanti, "Beyond Transplantation" *Arch. Surg.* 123,545-549 (1988), describe an approach for making new organs for transplantation. Vacanti, et al., recognized that cells require a matrix for attachment and support if they are to survive following implantation, that a minimum number of cells was essential for function in vivo, and that the matrix must be porous enough to allow nutrients and gases to reach all of the cells on and within the matrix by diffusion, until the matrix-cell structure was vascularized. They report that there are advantages to using synthetic biodegradable polymer substrates to form a scaffold that mimics its natural counterparts, the extracellular matrices (ECM) of the body, serving as both a physical support and an adhesive substrate for isolated parenchymal cells during in vitro culture, and subsequent implantation, degrading as the cells begin to secrete they own ECM support. These matrices have also been implanted and seeded directly, to form new tissues.

II. Cells to be Seeded onto/onto Decellularized Tissues

Human stem cells are totipotential or pluripotential precursor cells capable of generating a variety of mature human cell lineages. This ability serves as the basis for the cellular differentiation and specialization necessary for organ and tissue development. Recent success at transplanting such stem cells have provided new clinical tools to reconstitute and/or supplement the bone marrow after myeloablation due to disease, exposure to toxic chemical or radiation. Further evidence exists which demonstrates that stem cells can be employed to repopulate many, if not all, tissues and restore physiologic and anatomic functionality. The application of stem cells in tissue engineering, gene therapy delivery and cell therapeutics is also advancing rapidly.

Obtaining sufficient human stem cells has been problematic for several reasons. First, isolation of normally occurring populations of stem cells in adult tissues has been technically difficult, costly and very limited in quantity. Secondly, procurement of these cells from embryos or fetal tissue including abortuses has raised many ethical and moral concerns. The widely held belief that the human embryo and fetus constitute independent life has justified a moratorium on the use of such sources for any purpose. Alternative sources which do not violate the sanctity of independent life are essential for further progress in the use of stem cells clinically.

Umbilical cord blood (cord blood) is a known source of hemopoietic pluripotent, progenitor stem cells that are cryopreserved for use in hemopoietic reconstitution. The use of cord blood for this purpose is well known and is becoming a widely used therapeutic procedure. The conventional technique for the collection of cord blood is based on the use of a needle or cannula which is used with the aid of gravity to drain the cord blood from the placenta. Usually the needle or cannula is placed in the umbilical vein and the placenta is gently massaged to aid in draining the cord blood from the placenta.

The Applicant has unexpectedly discovered that the placenta after birth contains quiescent cells which can be activated if the placenta is properly processed after birth. For example, after expulsion from the womb, the placenta is exsanguinated as quickly as possible to prevent or minimize apoptosis. Subsequently, as soon as possible after exsanguination the placenta is perfused to remove blood, residual cells, proteins, factors and any other materials present in the organ. Perfusion is normally continued with an appropriate perfusate for at least two to more than twenty-four hours. In several additional embodiments the placenta is perfused for at least 4, 6, 8, 10, 12, 14, 16, 18, 20, and 22 hours. In other words, this invention is based at least in part on the discovery that the cells of a post-partum placenta can be activated by exsanguination and perfusion for a sufficient amount of time. Therefore, the placenta can readily be used as a rich and abundant source of human placental stem cells, which cells can be used for research, including drug discovery, treatment and prevention of diseases, in particular transplantation surgeries or therapies, and the generation of committed cells, tissues and organoids.

Further, surprisingly and unexpectedly the human placental stem cells produced by the exsanguinated, perfused and/or cultured placenta are pluripotent stem cells that can readily be differentiated into any desired cell type.

The present invention relates to methods of treating and culturing an isolated placenta for use as a bioreactor for the production and propagation of embryonic-like stem cells originating from the placenta or from exogenous sources. The present invention also relates to the use of a cultured placenta as a bioreactor to produce biological materials, including, but not limited to, antibodies, hormones, cytokines, and growth factors. The present invention also relates to methods of collecting and isolating the stem cells and biological materials from the cultured placenta.

The present invention relates to methods of perfusing and exsanguinating an isolated placenta once it has been expunged from a uterus, to remove all residual cells. The invention further relates to culturing the isolated and exsanguinated placenta under the appropriate conditions to allow for the production and propagation of embryonic-like stem cells.

The present invention provides a method of extracting and recovering embryonic-like stem cells, including, but not limited to pluripotent or multipotent stem cells, from an exsanguinated human placenta. Embryonic-like stem cells have characteristics of embryonic stem cells but are not derived from the embryo. Such cells are as versatile (e.g., pluripotent) as human embryonic stem cells. According to the methods of the invention, human placenta is used post-birth as the source of embryonic-like stem cells.

According to the methods of the invention embryonic-like stem cells are extracted from a drained placenta by means of a perfusion technique that utilizes either or both of the umbilical artery and umbilical vein. The placenta is preferably drained by exsanguination and collection of residual blood (e.g., residual umbilical cord blood). The drained placenta is then processed in such a manner as to establish an ex vivo, natural bioreactor environment in which resident embryonic-like stem cells within the parenchyma and extravascular space are recruited. The embryonic-like stem cells migrate into the drained, empty microcirculation where, according to the methods of the invention, they are collected, preferably by washing into a collecting vessel by perfusion.

Methods of Isolating and Culturing Placenta

The following discloses, among other things, the method of collecting placental stem cells and other multipotent stem cells from a placenta. The present applicant describes this method in detail in applicant's pending U.S. patent application Ser. No. 10/004,942, filed Dec. 5, 2001, claiming priority to U. S. Provisional Patent Application No. 60/251, 900, filed Dec. 6, 2000, and wherein pending U.S. patent application Ser. No. 10/004,942 is incorporated herein by reference in this application.

Pretreatment of Placenta

According to the methods of the invention, a placenta (for example, a human placenta) is recovered shortly after its expulsion after birth and, in certain embodiments, the cord blood in the placenta is recovered. In certain embodiments, the placenta is subjected to a conventional cord blood recovery process. Such cord blood recovery may be obtained commercially, such as for example Lifebank Services, Bethesda, Md. The cord blood can be drained shortly after expulsion of the placenta. Alternatively, the placenta can be stored, preferably for no longer than 48 hours, prior to the collection of cord blood.

The placenta is preferably recovered after expulsion under aseptic conditions, and stored in an anticoagulant solution at a temperature of 5 to 25 degrees C. (centigrade). Suitable anticoagulant solutions are well known in the art. For example, a solution of heparin or warfarin sodium can be used. In a preferred embodiment, the anticoagulant solution comprises a solution of heparin (1% w/w in 1:1000 solution). The drained placenta is preferably stored for no more than 36 hours before the embryonic-like stem cells are collected. The solution which is used to perfuse the placenta to remove residual cells can be the same solution used to perfuse and culture the placenta for the recovery of stem cells. Any of these perfusates may be collected and used as a source of embryonic-like stem cells.

In certain embodiments, the proximal umbilical cord is clamped, preferably within 4-5 cm (centimeter) of the insertion into the placental disc prior to cord blood recovery. In other embodiments, the proximal umbilical cord is clamped after cord blood recovery but prior to further processing of the placenta.

Conventional techniques for the collection of cord blood may be used. Typically a needle or cannula is used, with the aid of gravity, to drain cord blood from (i.e., exsanguinate) the placenta (Boyse et al., U.S. Pat. No. 5,192,553, issued Mar. 9, 1993; Anderson, U.S. Pat. No. 5,372,581, entitled Method and apparatus for placental blood collection, issued Dec. 13, 1994; Hessel et al., U.S. Pat. No. 5,415,665, entitled Umbilical cord clamping, cutting, and blood collecting device and method, issued May 16, 1995). The needle or cannula is usually placed in the umbilical vein and the placenta is gently massaged to aid in draining cord blood from the placenta.

Typically, a placenta is transported from the delivery or birthing room to another location, e.g., a laboratory, for recovery of the cord blood and/or drainage and perfusion. The placenta is preferably transported in a sterile, thermally insulated transport device (maintaining the temperature of the placenta between 20-28EC), for example, by placing the placenta, with clamped proximal umbilical cord, in a sterile zip-lock plastic bag, which is then placed in an insulated container, as shown in FIGS. 2a-e.

In a preferred embodiment, the placenta is recovered from a patient by informed consent and a complete medical history of the patient prior to, during and after pregnancy is also taken and is associated with the placenta. These medical records can be used to coordinate subsequent use of the placenta or the stem cells harvested therefrom. For example, the human placental stem cells can then easily be used for personalized medicine for the infant in question, the parents, siblings or other relatives. Indeed, the human placental stem cells are more versatile than cord blood. However, it should be noted that the invention includes the addition of human placental stem cells produced by the exsanguinated, perfused and/or cultured placenta to cord blood from the same or different placenta and umbilical cord. The resulting cord blood will have an increased concentration/population of human stem cells and thereby is more useful for transplantation e.g. for bone marrow transplantations.

Exsanguination of Placenta and Removal of Residual Cells

The invention provides a method for recovery of stem or progenitor cells, including, but not limited to embryonic-like stem cells, from a placenta that is exsanguinated, i.e., completely drained of the cord blood remaining afterbirth and/or a conventional cord blood recovery procedure. According to the methods of the invention, the placenta is exsanguinated and perfused with a suitable aqueous perfusion fluid, such as an aqueous isotonic fluid in which an anticoagulant (e.g., heparin, warfarin sodium) is dissolved. Such aqueous isotonic fluids for perfusion are well known in the art, and include, e.g., a 0.9 N sodium chloride solution. The perfusion fluid preferably comprises the anticoagulant, such as heparin or warfarin sodium, at a concentration that is sufficient to prevent the formation of clots of any residual cord blood. In a specific embodiment, a concentration of from 100 to 1000 units of heparin is employed. In one embodiment, apoptosis inhibitors can be used during and immediately after exsanguination and then these agents can be washed from the placenta.

According to the methods of the invention, the placenta is exsanguinated by passage of the perfusion fluid through either or both of the umbilical artery and umbilical vein, using a gravity flow into the placenta. The placenta is preferably oriented (e.g., suspended) in such a manner that the umbilical artery and umbilical vein are located at the highest point of the placenta. In a preferred embodiment, the umbilical artery and the umbilical vein are connected simultaneously, as shown in FIG. 1, to a pipette that is connected via a flexible connector to a reservoir of the perfusion fluid. The perfusion fluid is passed into the umbilical vein and artery and collected in a suitable open vessel from the surface of the placenta that was attached to the uterus of the mother during gestation.

In a preferred embodiment, the proximal umbilical cord is clamped during perfusion, and more preferably, is clamped within 4-5 cm (centimeter) of the cord's insertion into the placental disc.

In one embodiment, a sufficient amount of perfusion fluid is used that will result in removal of all residual cord blood and subsequent collection or recovery of placental cells, including but not limited to embryonic-like stem cells and progenitor cells, that remain in the placenta after removal of the cord blood.

It has been observed that when perfusion fluid is first collected from a placenta during the exsanguination process, the fluid is colored with residual red blood cells of the cord blood. The perfusion fluid tends to become clearer as perfusion proceeds and the residual cord blood cells are washed out of the placenta. Generally from 30 to 100 ml (milliliter) of perfusion fluid is adequate to exsanguinate the placenta and to recover an initial population of embryonic-like cells from the placenta, but more or less perfusion fluid may be used depending on the observed results.

Culturing Placenta

After exsanguination and perfusion of the placenta, the embryonic-like stem cells are observed to migrate into the exsanguinated and perfused microcirculation of the placenta where, according to the methods of the invention, they are collected, preferably by washing into a collecting vessel by perfusion. Perfusing the isolated placenta not only serves to remove residual cord blood but also provide the placenta with the appropriate nutrients, including oxygen.

In certain embodiments of the invention, the drained, exsanguinated placenta is cultured as a bioreactor, i.e., an ex vivo system for propagating cells or producing biological materials. The number of propagated cells or level of biological material produced in the placental bioreactor is maintained in a continuous state of balanced growth by periodically or continuously removing a portion of a culture medium or perfusion fluid that is introduced into the placental bioreactor, and from which the propagated cells or the produced biological materials may be recovered. Fresh medium or perfusion fluid is introduced at the same rate or in the same amount.

The number and type of cells propagated may easily be monitored by measuring changes in morphology and cell surface markers using standard cell detection techniques such as flow cytometry, cell sorting, immunocytochemistry (e.g., staining with tissue specific or cell-marker specific antibodies), fluorescence activated cell sorting (FACS), magnetic activated cell sorting (MACS), by examination of the morphology of cells using light or confocal microscopy, or by measuring changes in gene expression using techniques well known in the art, such as PCR and gene expression profiling.

In one embodiment, the cells may be sorted using a fluorescence activated cell sorter (FACS). Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In another embodiment, magnetic beads can be used to separate cells. The cells may be sorted using a magnetic activated cell sorting (MACS) technique, a method for separating particles based on their ability to bind magnetic beads (0.5-100 µm diameter). A variety of useful modifications can be performed on the magnetic microspheres, including covalent addition of antibody which specifically recognizes a cell-solid phase surface molecule or hapten. A magnetic field is then applied, to physically manipulate the selected beads. The beads are then mixed with the cells to allow binding. Cells are then passed through a magnetic field to separate out cells having cell surface markers. These cells can then isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation.

In preferred embodiments, the placenta to be used as a bioreactor is exsanguinated and washed under sterile conditions so that any adherent coagulated and non-adherent cellular contaminants are removed. The placenta is then cultured or cultivated under aseptic conditions in a container or other suitable vessel, and perfused with perfusate solution (e.g., a normal saline solution such as phosphate buffered saline (PBS)) with or without an anticoagulant (e.g., such as for example,heparin or warfarin sodium), and/or with or without an antimicrobial agent (e.g., such as antibiotics).

The effluent perfusate comprises both circulated perfusate, which has flowed through the placental circulation, and extravasated perfusate, which exudes from or passes through the walls of the blood vessels into the surrounding tissues of the placenta. The effluent perfusate is collected, and preferably, both the circulated and extravasated perfusates are collected, preferably in a sterile receptacle. Alterations in the conditions in which the placenta is maintained and the nature of the perfusate can be made to modulate the volume and composition of the effluent perfusate.

Cell types are then isolated from the collected perfusate by employing techniques known by those skilled in the art, such as for example, but not limited to density gradient centrifugation, magnet cell separation, flow cytometry, affinity cell separation or differential adhesion techniques.

Figure 3:
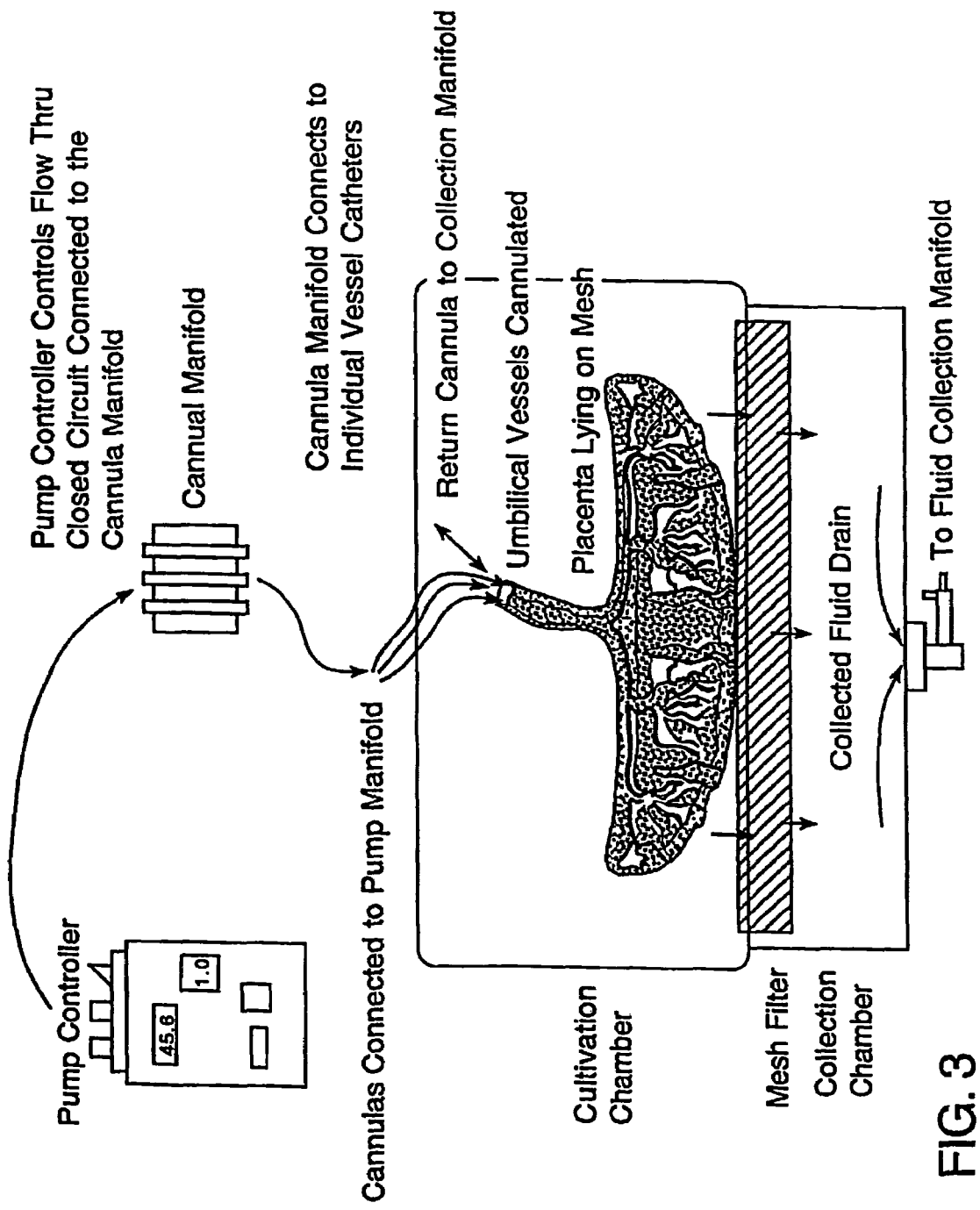
FIG. 3 is a cross-sectional schematic of a perfused placenta in a device for use as a bioreactor.

In one embodiment, a placenta is placed in a sterile basin and washed with 500 ml of phosphate-buffered normal saline. The wash fluid is then discarded. The umbilical vein is then cannulated with a cannula, e.g., a TEFLON7 or plastic cannula, that is connected to a sterile connection apparatus, such as sterile tubing. The sterile connection apparatus is connected to a perfusion manifold, as shown in FIG. 3. The container containing the placenta is then covered and the placenta is maintained at room temperature (20-25 degrees C.) for a desired period of time, preferably from 2 to 24 hours, and preferably, no longer than 48 hours. The placenta may be perfused continually, with equal volumes of perfusate introduced and effluent perfusate removed or collected. Alternatively, the placenta may be perfused periodically, e.g., for example, at every 2 hours or at 4, 8, 12, and 24 hours, with a volume of perfusate, e.g., preferably, 100 ml of perfusate (sterile normal saline supplemented with or without 1000 µ/l heparin and/or EDTA and/or CPDA (creatine phosphate dextrose)). In the case of periodic perfusion, preferably equal volumes of perfusate are introduced and removed from the culture environment of the placenta, so that a stable volume of perfusate bathes the placenta at all times.

The effluent perfusate that escapes the placenta, e.g., at the opposite surface of the placenta, is collected and processed to isolate embryonic-like stem cells, progenitor cells or other cells of interest.

Various media may be used as perfusion fluid for culturing or cultivating the placenta, such as DMEM, F-12, M199, RPMI, Fisher's, Iscore's, McCoy's and combinations thereof, supplemented with fetal bovine serum (FBS), whole human serum (WHS), or human umbilical cord serum collected at the time of delivery of the placenta.

In certain embodiments, the embryonic-like stem cells are induced to propagate in the placenta bioreactor by introduction of nutrients, hormones, vitamins, growth factors, or any combination thereof, into the perfusion solution. Serum and other growth factors may be added to the propagation perfusion solution or medium. Growth factors are usually proteins and include for example, but are not limited to: cytokines, lymphokines, interferons, colony stimulating factors (CSF's), interferons, chemokines, and interleukins. Other growth factors that may be used include recombinant human hematopoietic growth factors including, for example, ligands, stem cell factors, thrombopoeitin (Tpo), interleukins, and granulocyte colony-stimulating factor (G-CSF).

The growth factors introduced into the perfusion solution can stimulate the propagation of undifferentiated embryonic-like stem cells, committed progenitor cells, or differentiated cells (e.g., differentiated hematopoietic cells). The growth factors can stimulate the production of biological materials and bioactive molecules including for example, but not limited to, immunoglobulins, hormones, enzymes or growth factors as previously described.

In one embodiment of the invention, the placenta is used as a bioreactor for propagating endogenous cells (i.e., cells that originate from the placenta), including but not limited to, various kinds of pluripotent and/or totipotent embryonic-like stem cells and lymphocytes. To use the placenta as a bioreactor, it may be cultured for varying periods of time under sterile conditions by perfusion with perfusate solution as disclosed herein. In specific embodiments, the placenta is cultured for at least 12, 24, 36, or 48 hours, or for 3-5 days, 6-10 days, or for one to two weeks. In a preferred embodiment, the placenta is cultured for 48 hours. The cultured placenta should be "fed" periodically to remove the spent media, depopulate released cells, and add fresh media. The cultured placenta should be stored under sterile conditions to reduce the possibility of contamination, and maintained under intermittent and periodic pressurization to create conditions that maintain an adequate supply of nutrients to the cells of the placenta. It should be recognized that the perfusing and culturing of the placenta can be both automated and computerized for efficiency and increased capacity.

In another embodiment, the placenta is processed to remove all endogenous proliferating cells, such as embryonic-like stem cells, and to allow foreign (i.e., exogenous) cells to be introduced and propagated in the environment of the perfused placenta. The invention contemplates a large variety of stem or progenitor cells that can be cultured in the placental bioreactor, including for example, but not limited to, embryonic-like stem cells, mesenchymal stem cells, stromal cells, endothelial cells, hepatocytes, keratinocytes, and stem or progenitor cells for a particular cell type, tissue or organ, including for example, but not limited to neurons, myelin, muscle, blood, bone marrow, skin, heart, connective tissue, lung, kidney, liver, and pancreas (e.g., pancreatic islet cells).

Sources of mesenchymal stem cells include bone marrow, embryonic yolk sac, placenta, umbilical cord, fetal and adolescent skin, and blood. Bone marrow cells may be obtained from iliac crest, femora, tibiae, spine, rib or other medullary spaces.

Methods for the selective destruction, ablation or removal of proliferating or rapidly dividing cells from a tissue or organ are well-known in the art, e.g., methods of cancer or tumor treatment. For example, the perfused placenta may be irradiated with electromagnetic, V, X-ray, gamma- or beta-radiation to eradicate all remaining viable, endogenous cells. The foreign cells to be propagated are introduced into the irradiated placental bioreactor, for example, by perfusion.

Collection of Cells from the Placenta

As disclosed above, after exsanguination and perfusion of the placenta, embryonic-like stem cells migrate into the drained, empty microcirculation where, according to the methods of the invention, they are collected, preferably by collecting the effluent perfusate in a collecting vessel.

Figure 4:
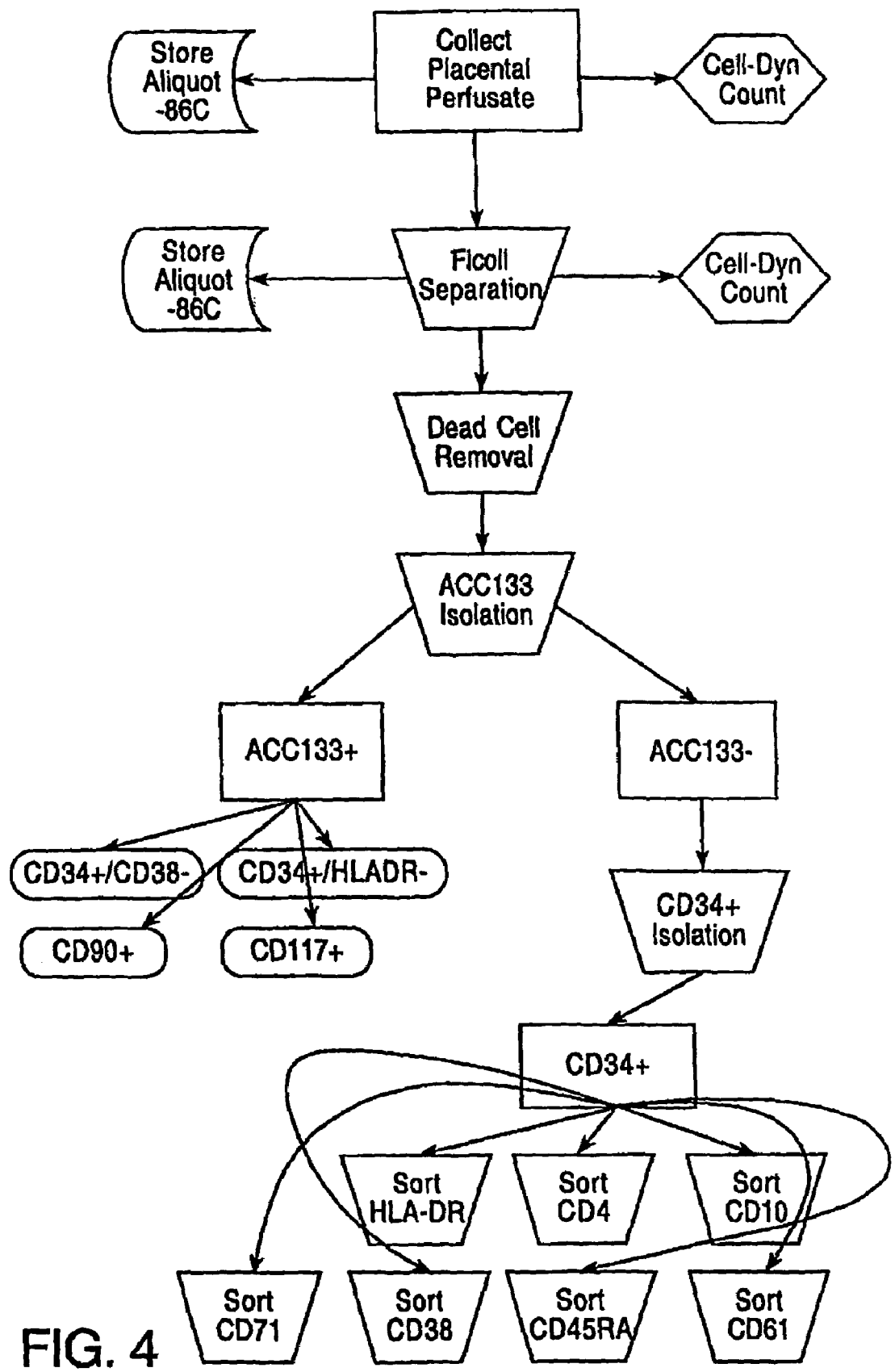
FIG. 4 is a selection scheme for sorting cells retrieved from a perfused placenta.

In preferred embodiments, cells cultured in the placenta are isolated from the effluent perfusate using techniques known by those skilled in the art, such as, for example, density gradient centrifugation, magnet cell separation, flow cytometry, or other cell separation or sorting methods well known in the art, and sorted, for example, according to the scheme shown in FIG. 4.

In a specific embodiment, cells collected from the placenta are recovered from the effluent perfusate by centrifugation at X 00×g for 15 minutes at room temperature, which separates cells from contaminating debris and platelets. The cell pellets are resuspended in IMDM serum-free medium containing 2 U/ml heparin and 2 mM EDTA (GibcoBRL, NY). The total mononuclear cell fraction was isolated using Lymphoprep (Nycomed Pharna, Oslo, Norway) according to the manufacturer's recommended procedure and the mononuclear cell fraction was resuspended. Cells were counted using a hemocytometer. Viability was evaluated by trypan blue exclusion. Isolation of cells is achieved by "differential trypsinization", using a solution of 0.05% trypsin with 0.2% EDTA (Sigma, St. Louis Mo.). Differential trypsinization was possible because fibroblastoid cells detached from plastic surfaces within about five minutes whereas the other adherent populations required more than 20-30 minutes incubation. The detached fibroblastoid cells were harvested following trypsinization and trypsin neutralization, using Trypsin Neutralizing Solution (TNS, BioWhittaker). The cells were washed in H.DMEM and resuspended in MSCGM.

In another embodiment, the isolated placenta is perfused for a period of time without collecting the perfusate, such that the placenta may be perfused for 2, 4, 6, 8, 10, 12, 20 and 24 hours or even days before the perfusate is collected.

In another embodiment, cells cultured in the placenta bioreactor are isolated from the placenta by physically dissecting the cells away from the placenta.

In another embodiment, cells cultured in the placenta bioreactor are isolated from the placenta by dissociating the tissues of the placenta or a portion thereof, and recovering the cultured cells by art-known cell separation or sorting methods such as density gradient centrifugation, magnet cell separation, flow cytometry, etc.

In a preferred embodiment, perfusion of the placenta and collection of effluent perfusate is repeated once or twice during the culturing of the placenta, until the number of recovered nucleated cells falls below 100 cells/ml. The perfusates are pooled and subjected to light centrifugation to remove platelets, debris and de-nucleated cell membranes. The nucleated cells are then isolated by Ficoll-Hypaque density gradient centrifugation and after washing, resuspended in H.DMEM. For isolation of the adherent cells, aliquots of 5-10×10$^6$ cells are placed in each of several T-75 flasks and cultured with commercially available Mesenchymal Stem Cell Growth Medium (MSCGM) obtained from BioWhittaker, and placed in a tissue culture incubator (37EC, 5% $CO_2$). After 10 to 15 days, non-adherent cells are removed from the flasks by washing with PBS. The PBS is then replaced by MSCGM. Flasks are preferably examined daily for the presence of various adherent cell types and in particular, for identification and expansion of clusters of fibroblastoid cells.

In other embodiments, the cells collected from the placenta are cryopreserved for use at a later time. Methods for cryopreservation of cells, such as stem cells, are well known in the art, for example, cryopreservation using the methods of Boyse et al. U.S. Pat. No. 5,192,553, issued Mar. 9, 1993) or Hu et al. (WO 00/73421, published Dec. 7, 2000).

Cell Populations Obtained from or Cultured in Placenta

Embryonic-like stem cells obtained in accordance with the methods of the invention may include pluripotent cells, i.e., cells that have complete differentiation versatility, that are self-renewing, and can remain dormant or quiescent within tissue. The embryonic-like stem cells can also include multipotent cells, committed progenitor cells, or fibroblastoid cells.

In a preferred embodiment, embryonic-like stem cells obtained by the methods of the invention are viable, quiescent, pluripotent stem cells that exist within a full-tern human placenta and that can be recovered following successful birth and placental expulsion, resulting in the recovery of as many as one billion nucleated cells, which yield 50-100 million multipotent and pluripotent stem cells.

The human placental stem cells provided by the placenta are surprisingly embryonic-like, for example, the presence or absence of the following cell surface markers have been identified for these cells: SSEA3$^-$, SSEA4$^+$, Oct-4$^+$ and ABC-p$^+$. Thus, the invention encompasses stem cells which have not been isolated or otherwise obtained from an embryonic source but which can be identified by the presence or absence of the following markers: SSEA3$^-$, SSEA4$^-$, Oct-4$^-$ and ABC-p$^-$. In one embodiment, the human placental stem cells do not express MHC Class 2 antigens.

The stem cells isolated from the placenta are homogenous, and sterile. Further, the stem cells are readily obtained in a form suitable for administration to humans, i.e., they are of pharmaceutical grade.

Preferred embryonic-like stem cells obtained by the methods of the invention may be identified by the presence of the following cell surface markers: CD10+, CD29+, CD34−, CD44+, CD45−, CD54+, CD90+, SH2+, SH3+, SH4+, SSEA3−, SSEA4−, OCT-4+, and ABC-p+. Such cell surface markers are routinely determined according to methods well known in the art, e.g. by flow cytometry, followed by washing and staining with an anti-cell surface marker antibody. For example, to determine the presence of CD-34 or CD-38, cells may be washed in PBS and then double-stained with anti-CD34 phycoerythrin and anti-CD38 fluorescein isothiocyanate (Becton Dickinson, Mountain View, Calif.).

The embryonic-like stem cells obtained by the methods of the invention may be induced to differentiate along specific cell lineages, including adipogenic, chondrogenic, osteogenic, hematopoietic, myogenic, vasogenic, neurogenic, and hepatogenic. In certain embodiments, embryonic-like stem cells obtained according to the methods of the invention are induced to differentiate for use in transplantation and ex vivo treatment protocols In certain embodiments, embryonic-like stem cells obtained by the methods of the invention are induced to differentiate into a particular cell type and genetically engineered to provide a therapeutic gene product. In a specific embodiment, embryonic-like stem cells obtained by the methods of the invention are incubated with a compound in vitro that induces it to differentiate, followed by direct transplantation of the differentiated cells to a subject. Thus, the invention encompasses methods of differentiating the human placental stem cells using standard culturing media. Further, the invention encompasses hematopoietic cells, neuron cells, fibroblast cells, strand cells, mesenchymal cells and hepatic cells.

Embryonic-like stem cells may also be further cultured after collection from the placenta using methods well known in the art, for example, by culturing on feeder cells, such as irradiated fibroblasts, obtained from the same placenta as the embryonic-like stem cells or from other human or nonhuman sources, or in conditioned media obtained from cultures of such feeder cells, in order to obtain continued long-term cultures of embryonic-like stem cells. The embryonic-like stem cells may also be expanded, either within the placenta before collection from the placental bioreactor or in vitro after recovery from the placenta. In certain embodiments, the embryonic-like stem cells to be expanded are exposed to, or cultured in the presence of, an agent that suppresses cellular differentiation. Such agents are well-known in the art and include, but are not limited to, human Delta-1 and human Serrate-1 polypeptides (see, Sakano et al., U.S. Pat. No. 6,337,387 entitled "Differentiation-suppressive polypeptide", issued Jan. 8, 2002), leukemia inhibitory factor (LIF) and stem cell factor. Methods for the expansion of cell populations are also known in the art (see e.g., Emerson et al., U.S. Pat. No. 6,326,198 entitled "Methods and compositions for the ex vivo replication of stem cells, for the optimization of hematopoietic progenitor cell cultures, and for increasing the metabolism, GM-CSF secretion and/or IL-6 secretion of human stromal cells", issued Dec. 4, 2001; Kraus et al., U.S. Pat. No. 6,338,942, entitled "Selective expansion of target cell populations", issued Jan. 15, 2002).

The embryonic-like stem cells may be assessed for viability, proliferation potential, and longevity using standard techniques known in the art, such as trypan blue exclusion assay, fluorescein diacetate uptake assay, propidium iodide uptake assay (to assess viability); and thymidine uptake assay, MTT cell proliferation assay (to assess proliferation). Longevity may be determined by methods well known in the art, such as by determining the maximum number of population doubling in an extended culture.

In certain embodiments, the differentiation of stem cells or progenitor cells that are cultivated in the exsanguinated, perfused and/or cultured placenta is modulated using an agent or pharmaceutical compositions comprising a dose and/or doses effective upon single or multiple administration, to exert an effect sufficient to inhibit, modulate and/or regulate the differentiation of a cell collected from the placenta.

Agents that can induce stem or progenitor cell differentiation are well known in the art and include, but are not limited to, $Ca^{2+}$, EGF, aFGF, bFGF, PDGF, keratinocyte growth factor (KGF), TGF-β, cytokines (e.g., IL-1α, IL-1β, IFN-γ, TFN), retinoic acid, transferrin, hormones (e.g., androgen, estrogen, insulin, prolactin, triiodothyronine, hydrocortisone, dexamethasone), sodium butyrate, TPA, DMSO, NMF, DMF, matrix elements (e.g., collagen, laminin, heparan sulfate, MatrigelJ), or combinations thereof. In addition, compounds may be used to modulate differentiation of cells collected from the placenta.

Agents that suppress cellular differentiation are also well-known in the art and include, but are not limited to, human Delta-1 and human Serrate-1 polypeptides (see, Sakano et al., U.S. Pat. No. 6,337,387 entitled "Differentiation-suppressive polypeptide", issued Jan. 8, 2002), leukemia inhibitory factor (LIF), and stem cell factor.

The agent used to modulate differentiation can be introduced into the placental bioreactor to induce differentiation of the cells being cultured in the placenta. Alternatively, the agent can be used to modulate differentiation in vitro after the cells have been collected or removed from the placenta.

Determination that a stem cell has differentiated into a particular cell type may be accomplished by methods well-known in the art, e.g., measuring changes in morphology and cell surface markers using techniques such as flow cytometry or immunocytochemistry (e.g., staining cells with tissue-specific or cell-marker specific antibodies), by examination of the morphology of cells using light or confocal microscopy, or by measuring changes in gene expression using techniques well known in the art, such as PCR and gene-expression profiling.

In another embodiment, the cells cultured in the placenta are stimulated to produce bioactive molecules, such as immunoglobulins, hormones, enzymes.

In another embodiment, the cells cultured in the placenta are stimulated to proliferate, for example, by administration of erythropoietin, cytokines, lymphokines, interferons, colony stimulating factors (CSF's), interferons, chemokines, interleukins, recombinant human hematopoietic growth factors including ligands, stem cell factors, thrombopoeitin (Tpo), interleukins, and granulocyte colony-stimulating factor (G-CSF) or other growth factors.

In another embodiment, cells cultured in the placenta are genetically engineered either prior to, or after collection from, the placenta, using, for example, a viral vector such as an adenoviral or retroviral vector, or by using mechanical means such as liposomal or chemical mediated uptake of the DNA.

A vector containing a transgene can be introduced into a cell of interest by methods well known in the art, e.g., transfection, transformation, transduction, electroporation, infection, microinjection, cell fusion, DEAE dextran, calcium phosphate precipitation, liposomes, LIPOFECTIN, lysosome fusion, synthetic cationic lipids, use of a gene gun or a DNA vector transporter, such that the transgene is transmitted to daughter cells, e.g., the daughter embryonic-like stem cells or progenitor cells produced by the division of an embryonic-like stem cell. For various techniques for transformation or transfection of mammalian cells, see Keown et al., 1990, Methods Enzymol. 185: 527-37; Sambrook et al., 2001, Molecular Cloning, A Laboratory Manual, Third Edition, Cold Spring Harbor Laboratory Press, N.Y.

Preferably, the transgene is introduced using any technique, so long as it is not destructive to the cell's nuclear membrane or other existing cellular or genetic structures. In certain embodiments, the transgene is inserted into the nucleic genetic material by microinjection. Microinjection of cells and cellular structures is commonly known and practiced in the art.

For stable transfection of cultured mammalian cells, such as cells culture in a placenta, only a small fraction of cells may integrate the foreign DNA into their genome. The efficiency of integration depends upon the vector and transfection technique used. In order to identify and select integrants, a gene that encodes a selectable marker (e.g., for resistance to antibiotics) is generally introduced into the host embryonic-like stem cell along with the gene sequence of interest. Preferred selectable markers include those that confer resistance to drugs, such as G418, hygromycin and methotrexate. Cells stably transfected with the introduced nucleic acid can be identified by drug selection (e.g., cells that have incorporated the selectable marker gene will survive, while the other cells die). Such methods are particularly useful in methods involving homologous recombination in mammalian cells (e.g., in embryonic-like stem cells) prior to introduction or transplantation of the recombinant cells into a subject or patient.

A number of selection systems may be used to select transformed host embryonic-like cells. In particular, the vector may contain certain detectable or selectable markers. Other methods of selection include but are not limited to selecting for another marker such as: the herpes simplex virus thymidine kinase (Wigler et al., 1977, Cell 11: 223), hypoxanthine-guanine phosphoribosyltransferase (Szybalska and Szybalski, 1962, Proc. Natl. Acad. Sci. USA 48: 2026), and adenine phosphoribosyltransferase (Lowy et al., 1980, Cell 22: 817) genes can be employed in tk-, hgprt- or aprt- cells, respectively. Also, antimetabolite resistance can be used as the basis of selection for the following genes: dhfr, which confers resistance to methotrexate (Wigler et al., 1980, Proc. Natl. Acad. Sci. USA 77: 3567; O'Hare et al., 1981, Proc. Natl. Acad. Sci. USA 78: 1527); gpt, which confers resistance to mycophenolic acid (Mulligan and Berg, 1981, Proc. Natl. Acad. Sci. USA 78: 2072); neo, which confers resistance to the aminoglycoside G-418 (Colberre-Garapin et al., 1981, J. Mol. Biol. 150: 1); and hygro, which confers resistance to hygromycin (Santerre et al., 1984, Gene 30: 147).

The transgene may integrate into the genome of the cell of interest, preferably by random integration. In other embodiments the transgene may integrate by a directed method, e.g., by directed homologous recombination ("knock-in"), Chappel, U.S. Pat. No. 5,272,071; and PCT publication No. WO 91/06667, published May 16, 1991; U.S. Pat. No. 5,464,764; Capecchi et al., issued Nov. 7, 1995; U.S. Pat. No. 5,627,059, Capecchi et al. issued, May 6, 1997; U.S. Pat. No. 5,487,992, Capecchi et al., issued Jan. 30, 1996).

In a specific embodiment, the methods of Bonadio et al. (U.S. Pat. No. 5,942,496, entitled Methods and compositions for multiple gene transfer into bone cells, issued Aug. 24, 1999 and PCT WO95/22611, entitled "Methods and compositions for stimulating bone cells", published Aug. 24, 1995 ) are used to introduce nucleic acids into a cell of interest, such as a stem cell or progenitor cell cultured in the placenta, e.g., bone progenitor cells.

Uses of Cultured Placenta as a Bioreactor

Exsanguinated and/or cultured placental cells can be used as a bioreactor for the cultivation of cells, tissues, and organs. The placental mesoderm provides an ideal stromal environment, including an abundance of small molecules and growth factors, lipopolysaccharides, and extracellular matrix proteins, necessary for organogenesis and tissue neogenesis.

In one embodiment of the invention, the placenta can be populated with any particular cell type and used as a bioreactor for ex vivo cultivation of cells, tissues or organs. Such cells, tissue or organ cultures may be harvested used in transplantation and ex vivo treatment protocols. In this embodiment, the placenta is processed to remove all endogenous cells and to allow foreign (i.e., exogenous) cells to be introduced and propagated in the environment of the perfused placenta. Methods for removal of the endogenous cells are well-known in the art. For example, the perfused placenta is irradiated with electromagnetic, UV, X-ray, gamma- or beta-radiation to eradicate all remaining viable, endogenous cells. The foreign cells of interest to be propagated in the irradiated placental bioreactor are then introduced, for example, by introducing the cells via perfusion, via the vasculature or by direct injection into the placenta.

In another embodiment, the bioreactor may be used to produce and propagate novel chimeric cells, tissues, or organs. Such chimeras may be created using placental cells and one or more additional cell types as starting materials in a bioreactor. The interaction, or "cross-talk" between the different cell types can induce expression patterns distinct from either of the starting cell types. In one embodiment, for example, an autologous chimera is generated by propagating a patient=s autologous placental cells in a bioreactor with another cell type derived from the same patient. In another embodiment, for example, a heterologous chimera may be generated by addition of a patient=s cells, i.e., blood cells, to a bioreactor having heterologous placental cells. In yet another embodiment, the placental cells may be derived from a patient, and a second cell type from a second patient. Chimeric cells are then recovered having a different phenotypic and/or genetic characteristics from either of the starting cells. In a specific embodiment, the heterologous cells are of the same haplotype, and the chimeric cells are reintroduced into the patient.

In other embodiments, the bioreactor may be used for enhanced growth of a particular cell type, whether native or synthetic in origin. In another embodiment of the invention, the placenta is used as a bioreactor for propagating endogenous cells (i e., cells that originate from the placenta), including but not limited to, various kinds of pluripotent and/or totipotent embryonic-like stem cells and lymphocytes. In one embodiment, the placenta is incubated for varying periods of time with perfusate solution as disclosed herein. Such endogenous cells of placental origin may be transformed to recombinantly express a gene of interest, to express mutations, and/or may be engineered to delete a genetic locus, using "knock out" technology. For example, an endogenous target gene may be deleted by inactivating or "knocking out" the target gene or its promoter using targeted homologous recombination (e.g., see Smithies, et al., 1985, Nature 317, 230-234; Thomas & Capecchi, 1987, Cell 51, 503-512; Thompson, et al., 1989, Cell 5, 313-321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches may be used to remove, replace, or alter gene expression of interest in cells, tissue, and/or organs. This approach may be used to alter the phenotype of a cell, tissue, or organ, which may then be introduced into a human subject.

In other embodiments, a placenta cell may be induced to differentiate into a particular cell type, either ex vivo or in vivo. For example, pluripotent embryonic-like stem cells may be injected into a damaged organ, and for organ neogenesis and repair of injury in vivo. Such injury may be due to such conditions and disorders including, but not limited to, myocardial infarction, seizure disorder, multiple sclerosis, stroke, hypotension, cardiac arrest, ischemia, inflammation, age-related loss of cognitive function, radiation damage, cerebral palsy, neurodegenerative disease, Alzheimer's disease, Parkinsons's disease, Leigh disease, AIDS dementia, memory loss, amyotrophic lateral sclerosis, ischemic renal disease, brain or spinal cord trauma, heart-lung bypass, glaucoma, retinal ischemia, or retinal trauma.

The embryonic-like stem cells isolated from the placenta may be used, in specific embodiments, in autologous or heterologous enzyme replacement therapy to treat specific diseases or conditions, including, but not limited to lysosomal storage diseases, such as Tay-Sachs, Niemann-Pick, Fabry's, Gaucher's, Hunter's, Hurler's syndromes, as well as other gangliosidoses, mucopolysaccharidoses, and glycogenoses.

In other embodiments, the cells may be used as autologous or heterologous transgene carriers in gene therapy to correct inborn errors of metabolism or to treat cancer, tumors or other pathological conditions.

In other embodiments, the cells may be used in autologous or heterologous tissue regeneration or replacement therapies or protocols, including, but not limited to treatment of corneal epithelial defects, cartilage repair, facial dermabrasion, mucosal membranes, tympanic membranes, intestinal linings, neurological structures (e.g., retina, auditory neurons in basilar membrane, olfactory neurons in olfactory epithelium), burn and wound repair for traumatic injuries of the skin, or for reconstruction of other damaged or diseased organs or tissues.

The embryonic-like stem cells, progenitor cells, foreign cells, or engineered cells obtained from a placenta according to the methods of the invention can be used in the manufacture of a tissue or organ in vivo. The methods of the invention encompass using cells obtained from the placenta, e.g., embryonic-like stem cells, progenitor cells, or foreign stem or progenitor cells, to seed a matrix and to be cultured under the appropriate conditions to allow the cells to differentiate and populate the matrix. The tissues and organs obtained by the methods of the invention may be used for a variety of purposes, including research and therapeutic purposes.

Use of Embryonic-like Stem Cells

The embryonic-like stem cells of the invention can be used for a wide variety of therapeutic protocols in which a tissue or organ of the body is augmented, repaired or replaced by the engraftment, transplantation or infusion of a desired cell population, such as a stem cell or progenitor cell population. The embryonic-like stem cells of the invention can be used to replace or augment existing tissues, to introduce new or altered tissues, or to join together biological tissues or structures.

For example, embryonic-like stem cells of the invention can be used in therapeutic transplantation protocols, e.g., to augment or replace stem or progenitor cells of organs or tissues such as the liver, pancreas, kidney, lung, nervous system, muscular system, bone, bone marrow, thymus, spleen, mucosal tissue, gonads, or hair.

Embryonic-like stem cells may be used instead of specific classes of progenitor cells (e.g., chondrocytes, hepatocytes, hematopoietic cells, pancreatic parenchymal cells, neuroblasts, muscle progenitor cells, etc.) in therapeutic or research protocols in which progenitor cells would typically be used.

Embryonic-like stem cells of the invention can be used for augmentation, repair or replacement of cartilage, tendon, or ligaments. For example, in certain embodiments, prostheses (e.g., hip prostheses) are coated with replacement cartilage tissue constructs grown from embryonic-like stem cells of the invention. In other embodiments, joints (e.g., knee) are reconstructed with cartilage tissue constructs grown from embryonic-like stem cells. Cartilage tissue constructs can also be employed in major reconstructive surgery for different types of joints (for protocols, see e.g., Resnick, D., and Niwayama, G., eds., 1988, Diagnosis of Bone and Joint Disorders, 2d ed., W. B. Saunders Co.).

The embryonic-like stem cells of the invention can be used to repair damage of tissues and organs resulting from disease. In such an embodiment, a patient can be administered embryonic-like stem cells to regenerate or restore tissues or organs which have been damaged as a consequence of disease, e.g., enhance immune system following chemotherapy or radiation, repair heart tissue following myocardial infarction.

In other embodiments, the cells may be used in autologous or heterologous tissue regeneration or replacement therapies or protocols, including, but not limited to treatment of corneal epithelial defects, cartilage repair, facial dermabrasion, mucosal membranes, tympanic membranes, intestinal linings, neurological structures (e.g., retina, auditory neurons in basilar membrane, olfactory neurons in olfactory epithelium), burn and wound repair for traumatic injuries of the skin, scalp (hair) transplantation, or for reconstruction of other damaged or diseased organs or tissues.

EXAMPLES

Example 1

Analysis of Cell Types Recovered from Perfusate of Drained Placenta

This example describes the analysis of the cell types recovered from the effluent perfusate of a placenta cultured according to the methods of the invention.

Twenty ml of phosphate buffered saline solution (PBS) was added to the perfusion liquid and a 10 ml portion was collected and centrifuged for 25 minutes at 3000 rpm (revolutions per minute). The effluent was divided into four tubes and placed in an ice bath. 2.5 ml of a 1% fetal calf serum (FCS) solution in PBS was added and the tubes were centrifuged (140 minutes×10 g (acceleration due to gravity)). The pellet was resuspended in 5 ml of 1% FCS and two tubes were combined. The total mononucleocytes were calculated by adding the total lymphocytes and the total monocytes, and then multiplying the result by the total cell suspension volume.

The following table discloses the types of cells obtained by perfusion of a cultured placenta according to the methods described hereinabove.

| | WBC 1000/ml | Lym % | MID % | GRA % | Total Volume | # of Cells |
|---|---|---|---|---|---|---|
| CB (Cord Blood) | 10.5 | 43.2 | 8 | 48.8 | 60 ml | $6.3 \times 10^8$ |
| PP (Placenta perfusate, room temperature) | 12.0 | 62.9 | 18.2 | 18.9 | 15 ml | $1.8 \times 10^8$ |
| $PP_2$ (Placenta perfusate, 37 degrees C.) | 11.7 | 56.0 | 19.2 | 24.8 | 30 ml | $3.5 \times 10^8$ |

Samples of PP were after Ficoll.

Total cell number of PP after Ficoll was $5.3 \times 10^8$ and number of CB before processing is $6.3 \times 10^8$. Lym % indicates percent of lymphocytes;

MID % indicates percent of midrange white blood cells; and GRA% indicates percent of granulocytes.

Example 2

Analysis of Cells Obtained by Perfusion and Incubation of Placenta

The following example describes an analysis of cells obtained by perfusion and incubation of placenta according to the methods of the invention.

Materials and Methods

Placenta donors were recruited from expectant mothers that enrolled in private umbilical cord blood banking programs and provided informed consent permitting the use of the exsanguinated placenta following recovery of cord blood for research purposes. All donor data is confidential. These donors also permitted use of blinded data generated from the normal processing of their umbilical cord blood specimens for cryopreservation. This allowed comparison between the composition of the collected cord blood and the effluent perfusate recovered using the experimental method described below.

Following exsanguination of cord blood from the umbilical cord and placenta, according to the methods described hereinabove, the placenta was placed in a sterile, insulated container at room temperature and delivered to the laboratory within 4 hours of birth. Placentas were discarded if, on inspection, they had evidence of physical damage such as fragmentation of the organ or avulsion of umbilical vessels. Placentas were maintained at room temperature (23 plus/minus 2 degrees C.) or refrigerated (4 degrees C.) in sterile containers for 2 to 20 hours. Periodically, the placentas were immersed and washed in sterile saline at 25 degrees plus/minus 3 degrees C. to remove any visible surface blood or debris.

The umbilical cord was transected approximately 5 cm from its insertion into the placenta and the umbilical vessels were cannulated with TEFLON or polypropylene catheters connected to a sterile fluid path allowing bi-directional perfusion of the placenta and recovery of the effluent fluid. The methods described hereinabove enabled all aspects of placental conditioning, perfusion and effluent collection to be performed under controlled ambient atmospheric conditions as well as real-time monitoring of intravascular pressure and flow rates, core and perfusate temperatures and recovered effluent volumes. A range of conditioning protocols were evaluated over a 24-hour postpartum period, and the cellular composition of the effluent fluid was analyzed by flow cytometry, light microscopy and colony forming unit assays.

Placental Conditioning

The donor placentas were processed at room temperature within 12 to 24 hours after delivery. Before processing, the membranes were removed and the maternal site washed clean of residual blood. The umbilical vessels were cannulated with catheters made from 20 gauge Butterfly needles use for blood sample collection.

The donor placentas were maintained under varying conditions in an attempt to simulate and sustain a physiologically compatible environment for the proliferation and recruitment of residual embryonic-like stem cells. The cannula was flushed with IMDM serum-free medium (Gibco-BRL, NY) containing 2 U/ml heparin (Elkins-Sinn, NJ). Perfusion of the placenta continued at a rate of 50 ml per minute until approximately 150 ml of perfusate was collected. This volume of perfusate was labeled "early fraction". Continued perfusion of the placenta at the same rate resulted in the collection of a second fraction of approximately 150 ml and was labeled "late fraction". During the course of the procedure, the placenta was gently massaged to aid in the perfusion process and assist in the recovery of cellular material. Effluent fluid was collected from the perfusion circuit by both gravity drainage and aspiration through the arterial cannula.

Placentas were then perfused with heparinized (2 U/ml) Dulbecco's modified Eagle Medium (H.DMEM) at the rate of 15 ml/minute for 10 minutes and the perfusates were collected from the maternal sites within one hour and the nucleated cells counted. The perfusion and collection procedures were repeated once or twice until the number of recovered nucleated cells fell below 100/ml. The perfusates were pooled and subjected to light centrifugation to remove platelets, debris and de-nucleated cell membranes. The nucleated cells were then isolated by Ficoll-Hypaque density gradient centrifugation and after washing, resuspended in H.DMEM. For isolation of the adherent cells, aliquots of $5-10 \times 10^6$ cells were placed in each of several T-75 flasks and cultured with commercially available Mesenchymal Stem Cell Growth Medium (MSCGM) obtained from BioWhittaker, and placed in a tissue culture incubator (37EC, 5% $CO_2$). After 10 to 15 days, the non-adherent cells were removed by washing with PBS, which was then replaced by MSCGM. The flasks were examined daily for the presence of various adherent cell types and in particular, for identification and expansion of clusters of fibroblastoid cells.

Cell recovery and Isolation

Cells were recovered from the perfusates by centrifugation at X 00×g for 15 minutes at room temperature. This procedure served to separate cells from contaminating debris and platelets. The cell pellets were resuspended in IMDM serum-free medium containing 2 U/ml heparin and 2 mM EDTA (GibcoBRL, NY). The total mononuclear cell fraction was isolated using Lymphoprep (Nycomed Pharma, Oslo, Norway) according to the manufacturer's recommended procedure and the mononuclear cell fraction was resuspended. Cells were counted using a hemocytometer. Viability was evaluated by trypan blue exclusion. Isolation of mesenchymal cells was achieved by "differential trypsinization", using a solution of 0.05% trypsin with 0.2% EDTA (Sigma, St. Louis Mo). Differential trypsinization was possible because fibroblastoid cells detached from plastic surfaces within about five minutes whereas the other adherent populations required more than 20-30 minutes incubation. The detached fibroblastoid cells were harvested following trypsinization and trypsin neutralization, using Trypsin Neutralizing Solution (TNS, BioWhittaker). The cells were washed in H.DMEM and resuspended in MSCGM.

Flow cytometry was carried out using a Becton-Dickinson FACSCalibur instrument and FITC and PE labeled monoclonal antibodies (mAbs), selected on the basis of known markers for bone marrow-derived MSC (mesenchymal stem cells), were purchased from B.D. and Caltag laboratories (South San Francisco, Calif.), and SH2, SH3 and SH4 antibody producing hybridomas were obtained from and reactivities of the mAbs in their cultured supernatants were detected by FITC or PE labeled F(ab)'2 goat anti-mouse antibodies. Lineage differentiation was carried out using commercially available induction and maintenance culture media (BioWhittaker), used as per manufacturer's instructions.

Isolation of Placental Embryonic-like Stem Cells

Microscopic examination of the adherent cells in the culture flasks revealed morphologically different cell types. Spindle-shaped cells, round cells with large nuclei and numerous perinuclear small vacuoles, and star-shaped cells with several projections (through one of which star-shaped cells were attached to the flask) were observed adhering to the culture flasks. Although no attempts were made to further characterize these adherent cells, similar cells were observed in the culture of bone marrow, cord and peripheral blood, and therefore considered to be non-stem cell-like in nature. The fibroblastoid cells, appearing last as clusters, were candidates for being MSC (mesenchymal stem cells) and were isolated by differential trypsinization and subcultured in secondary flasks. Phase microscopy of the rounded cells, after trypsinization, revealed that the cells were highly granulated; indistinguishable from the bone marrow-derived MSC produced in the laboratory or purchased from Bio-Whittaker. When subcultured, the placenta-derived embryonic-like stem cells, in contrast to their earlier phase, adhered within hours, assumed characteristic fibroblastoid shape, and formed a growth pattern identical to the reference bone marrow-derived MSC. During subculturing and refeeding, moreover, the loosely bound mononuclear cells were washed out and the cultures remained homogeneous and devoid of any visible non-fibroblastoid cell contaminants.

RESULTS

The expression of CD-34, CD-38, and other stem cell-associated surface markers on early and late fraction purified mononuclear cells was assessed by flow cytometry. Recovered, sorted cells were washed in PBS and then double-stained with antiCD34 phycoerythrin and anti-CD38 fluorescein isothiocyanate (Becton Dickinson, Mountain View, Calif.).

Cell isolation was achieved by using magnetic cell separation, such as for example, Auto Macs (Miltenyi). Preferably, CD 34+cell isolation is performed first.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

The foregoing description of a preferred embodiment of the invention has been presented for purposes of illustration and description. It is not intended to be exhaustive or to limit the invention precise form disclosed. Obvious modifications or variations are possible in light of the above teachings. All such obvious modifications and variations are intended to be within the scope of the appended claims.

What is claimed is:

1. A tissue matrix comprising placental stem cells, wherein the placental stem cells are $CD10^+$, $CD29^+$, $CD34^-$, $CD44^+$, $CD45^-$, $CD54^+$, $CD90^+$, $SH2^+$, $SH3^+$, and $SH4^+$; wherein said placental stem cells are additionally $OCT-4^+$, $SSEA3^-$ or $SSEA4^-$; and wherein said tissue matrix is made by a method comprising seeding human placental stem cells into or onto a decellularized or synthetic tissue matrix, wherein said stem cells are from a human placenta that has been drained of cord blood and perfused to remove residual blood.

2. A method of making a tissue matrix, comprising seeding human placental stem cells into or onto a decellularized or synthetic tissue matrix, wherein said stem cells are from a human placenta that has been drained of cord blood and perfused to remove residual blood, wherein said placental stem cells are $CD34^-$, $SSEA3^-$, $SSEA4^-$, and $OCT-4^+$.

3. A method of making a tissue matrix, comprising seeding human placental stem cells into or onto a decellularized or synthetic tissue matrix, wherein said stem cells are from a human placenta that has been drained of cord blood and perfused to remove residual blood, wherein said placental stem cells are $CD10^+$, $CD29^+$, $CD34^-$, $CD44^-$, $CD45^-$, $CD54^+$, $CD90^+$, $SH2^+$, $SH3^+$, and $SH4^+$; and wherein said placental stem cells are additionally $OCT-4^+$, $SSEA3^-$ or $SSEA4^-$.

4. A decellularized or synthetic tissue matrix comprising human placental stem cells, wherein the placental stem cells are $CD34^-$, $SSEA3^-$, $SSEA4^-$, and $OCT-4^+$.

5. A decellularized or synthetic tissue matrix comprising human placental stem cells, wherein the placental stem cells are $CD34^-$, $CD10^+$, $CD29^+$, $CD34^-$, $CD44^+$, $CD45^-$, $CD54^+$, $CD90^+$, $SH2^+$, $SH3^+$, and $SH4^+$; and wherein said placental stem cells are additionally $OCT-4^+$, $SSEA3^-$ or $SSEA4^-$.

* * * * *

UNITED STATES PATENT AND TRADEMARK OFFICE
CERTIFICATE OF CORRECTION

PATENT NO. : 7,311,904 B2 Page 1 of 1
APPLICATION NO. : 10/074976
DATED : December 25, 2007
INVENTOR(S) : Robert J. Hariri It is certified that error appears in the above-identified patent and that said Letters Patent is hereby corrected as shown below:

Column 27, line 21 Claim 1, replace "$CD44^-$" with --$CD44^+$--

Signed and Sealed this

Twentieth Day of May, 2008

JON W. DUDAS
*Director of the United States Patent and Trademark Office*

UNITED STATES PATENT AND TRADEMARK OFFICE
CERTIFICATE OF CORRECTION

PATENT NO. : 7,311,904 B2
APPLICATION NO. : 10/074976
DATED : December 25, 2007
INVENTOR(S) : Robert J. Hariri Page 1 of 1

It is certified that error appears in the above-identified patent and that said Letters Patent is hereby corrected as shown below:

Column 28, line 11, replace "$CD44^-$" with --$CD44^+$--

Column 28, line 20, delete the first instance of "$CD34^-$"

Signed and Sealed this

Twenty-fifth Day of November, 2008

JON W. DUDAS
*Director of the United States Patent and Trademark Office*